US008481078B2

(12) United States Patent
Holm et al.

(10) Patent No.: US 8,481,078 B2
(45) Date of Patent: *Jul. 9, 2013

(54) SOLID DOSAGE FORM COMPRISING A FIBRATE

(75) Inventors: Per Holm, Vanlose (DK); Tomas Norling, Lyngby (DK)

(73) Assignee: Veloxis Pharmaceuticals A/S, Horsholm (DK)

(*) Notice: Subject to any disclaimer, the term of this patent is extended or adjusted under 35 U.S.C. 154(b) by 0 days.

This patent is subject to a terminal disclaimer.

(21) Appl. No.: 13/315,030

(22) Filed: Dec. 8, 2011

(65) Prior Publication Data

US 2012/0195965 A1 Aug. 2, 2012

Related U.S. Application Data

(63) Continuation of application No. 12/642,563, filed on Dec. 18, 2009, now Pat. No. 8,124,125, which is a continuation of application No. 10/513,807, filed as application No. PCT/DK04/00667 on Oct. 1, 204, now Pat. No. 7,658,944.

(51) Int. Cl.
*A61K 9/20* (2006.01)

(52) U.S. Cl.
USPC .......................................................... 424/464

(58) Field of Classification Search
None
See application file for complete search history.

(56) References Cited

U.S. PATENT DOCUMENTS

| | | | |
|---|---|---|---|
| 4,603,143 A | 7/1986 | Schmidt | |
| 4,629,624 A * | 12/1986 | Grouiller et al. | 514/772.5 |
| 4,719,228 A | 1/1988 | Rawlins | |
| 4,800,079 A | 1/1989 | Boyer | |
| 4,816,264 A | 3/1989 | Phillips et al. | |
| 5,082,655 A | 1/1992 | Snipes et al. | |
| 6,027,747 A | 2/2000 | Terracol et al. | |
| 6,039,981 A | 3/2000 | Woo et al. | |
| 6,096,337 A | 8/2000 | Spireas et al. | |
| 6,277,405 B1 | 8/2001 | Stamm et al. | |
| 6,287,587 B2 | 9/2001 | Shigeyuki et al. | |
| 6,337,092 B1 | 1/2002 | Khan et al. | |
| 6,350,398 B1 | 2/2002 | Breitenbach et al. | |
| 6,372,251 B2 | 4/2002 | Liu et al. | |
| 6,569,463 B2 | 5/2003 | Patel et al. | |
| 7,022,337 B2 | 4/2006 | Liang et al. | |
| 7,217,431 B2 | 5/2007 | Holm et al. | |
| 7,255,877 B2 * | 8/2007 | Parikh | 424/489 |
| 7,658,944 B2 * | 2/2010 | Holm et al. | 424/464 |
| 8,124,125 B2 * | 2/2012 | Holm et al. | 424/464 |
| 2002/0056206 A1 | 5/2002 | Pace et al. | |
| 2002/0058065 A1 | 5/2002 | Guivarc'h et al. | |
| 2002/0119199 A1 | 8/2002 | Parikh | |
| 2002/0161032 A1 | 10/2002 | Guivarc'h et al. | |
| 2003/0077297 A1 | 4/2003 | Chen et al. | |
| 2003/0082215 A1 | 5/2003 | Lemut et al. | |
| 2003/0162827 A1 | 8/2003 | Venkataram et al. | |
| 2003/0180352 A1 | 9/2003 | Patel et al. | |
| 2003/0180367 A1 | 9/2003 | Parikh et al. | |
| 2004/0058005 A1 | 3/2004 | Stamm et al. | |
| 2005/0008704 A1 | 1/2005 | Ray et al. | |
| 2006/0222706 A1 | 10/2006 | Flashner-Barak et al. | |
| 2006/0222707 A1 | 10/2006 | Lerner et al. | |
| 2007/0015834 A1 | 1/2007 | Flashner-Barak et al. | |
| 2007/0148233 A1 | 6/2007 | Lerner et al. | |

FOREIGN PATENT DOCUMENTS

| | | |
|---|---|---|
| CA | 2253769 C | 9/2000 |
| DE | 2621873 A1 | 11/1977 |
| KR | 2001001249 A1 | 4/2003 |
| WO | WO-9311749 A1 | 6/1993 |
| WO | WO-9506460 | 3/1995 |
| WO | WO-0045817 A1 | 8/2000 |
| WO | WO-0050007 A1 | 8/2000 |
| WO | WO-0057918 A2 | 10/2000 |
| WO | WO-0134119 A2 | 5/2001 |
| WO | WO0195939 * | 12/2001 |
| WO | WO-0195939 A1 | 12/2001 |
| WO | WO-03004001 A1 | 1/2003 |
| WO | WO-03013608 A1 | 2/2003 |
| WO | WO-03103640 A1 | 12/2003 |
| WO | WO-2004041250 A2 | 5/2004 |
| WO | WO-2004073686 A2 | 9/2004 |
| WO | WO-2004073689 A1 | 9/2004 |
| WO | WO-2005004917 | 1/2005 |

OTHER PUBLICATIONS

Athyros et al. "Atorvastatin and Micronized Fenofibrate Alone and in Combination in Type 2 Diabetes with Combined Hyperlipidemia, Diabetes Care" 25: 1198-1202, 2002, printed pp. 1-13, especially p. 2, Research Design and Methods.

Lee, J. "Research Article: Drug nano- and microparticles processed into solid dosage forms: Physical Properties", Journal of Pharmaceutical Science, vol. 92, Issue 10, pp. 2057-2068, Published online: Jul. 30, 2003.

Office Action for U.S. Appl. No. 11/449,918 mailed Jan. 30, 2009; 23 pages.

Vasillios et al.: "Atorvastatin and Micronized Fenofibrate Alone and in Combination in Type 2 Diabetes with Combined Hyperlipidemia" Diabetes Care. 25: 1198-1202, 2002.

Center for Drug Evaluation and Research. Apr. 11, 2000. Application No. 19-304/5005. Tricor® (fenofibrate capsules), Final printed labeling.

Davidson, Michael H et al., "Abstract 5069: Atorvastatin/Fenofibrate 40/100 mg Fixed-Dose Combination tablet (LCP-AtorFen 40/100 mg) Offers Improved Efficacy over 40 mg Atorvastatin and Niger Dose 145 mg Fenofibrate in Patients with Dyslipidemia" Circulation 2008: 118:8-1139.

Sheu, et al., Int. J. Pharm. Int. J. Pharmaceuticals, vol. 102, No. 2. pp. 137-146.

* cited by examiner

Primary Examiner — Anand Desai
Assistant Examiner — Melissa Mercier
(74) Attorney, Agent, or Firm — Blank Rome LLP

(57) ABSTRACT

The invention provides stable, solid dosage forms and pharmaceutical compositions in particulate form comprising a fibrate, for example fenofibrate, dissolved in an non-aqueous vehicle in order to ensure improved bioavailability of the active ingredient upon oral administration relative to known fibrate formulations.

29 Claims, No Drawings

SOLID DOSAGE FORM COMPRISING A FIBRATE

This application is a continuation of U.S. patent application Ser. No. 12/642,563, filed on Dec. 18, 2009, now U.S. Pat. No. 8,124,125, which is a continuation of U.S. patent application Ser. No. 10/513,807, filed on Nov. 8, 2004, now U.S. Pat. No. 7,658,944, which is the U.S. national phase of International Patent Application No. PCT/DK04/000667, filed Oct. 1, 2004, which claims the benefit of Danish Patent Application Nos. PA 2003 01503, filed Oct. 10, 2003, PA 2004 00464, filed Mar. 23, 2004, and PA 2004 01006, filed Jun. 25, 2004. The contents of each of these applications is incorporated by reference herein in their entireties.

The present invention relates to novel solid dosage forms and pharmaceutical compositions comprising a fibrate, notably fenofibrate. Particularly, the invention discloses solid dosage forms having increased bioavailability. The solid dosage forms of the invention comprise fibrate dissolved in a suitable vehicle or mixture of vehicles. The dosage forms are especially intended for oral use and exhibit excellent storage stability, i.e. are stable. The invention also relates to methods for preparation of the solid dosage forms and pharmaceutical compositions and the use thereof.

BACKGROUND OF THE INVENTION

Fibrates are lipid regulating agents. Examples of fibrates include gemifibrozil, fenofibrate, bezafibrate, clofibrate and ciprofibrate. The compounds are regarded as prodrugs and are metabolised in vivo to their active metabolites. For illustrative purposes only, the following is based on a specific example of a fibrate, namely fenofibrate. Fenofibrate is chemically named 2-[4-(4-chlorobenzoyl]-2-methyl-propanoic acid, 1-methylethyl ester and has the following structural formula:

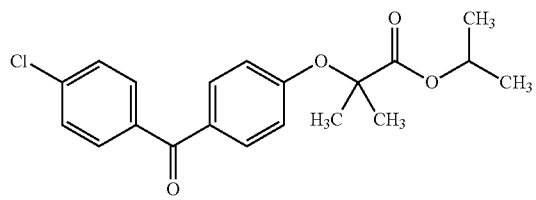 [SMILES: CC(C)OC(=O)C(C)(C)Oc1ccc(C(=O)c2ccc(Cl)cc2)cc1]

Fenofibrate is a white solid. The compound is insoluble in water. The melting point is 79-82° C. Fenofibrate is metabolised to the active substance fenofibric acid. Fenofibric acid has an elimination half-life of about 20 hours. Measurement of the detected amount of fenofibric acid in the blood of a patient can reflect the efficacy of fenofibrate uptake. Fenofibric acid produces reductions in total cholesterol (total-C), LDL-C, apo-lipoprotein B, total triglycerides, and triglyceride rich lipoprotein (VLDL) in treated patients. In addition, treatment with fenofibrate results in increases in high density lipoprotein (HDL) and apo-lipoprotein apoAI and apo AII. Fenofibrate acts as a potent lipid regulating agent offering unique and clinical advantages over existing products in the fibrate family of drug substances. Fenofibrate produces substantial reduction in plasma triglyceride levels in hypertriglyceridemic patients and in plasma cholesterol and LDL-C in hypercholesterolemic and mixed dyslipidemic patients.

Fenofibrate also reduces serum uric acid levels in hyperuricemic and normal subjects by increasing the urinary excretion of uric acid.

Clinical studies have demonstrated that elevated levels of total cholesterol, low density lipoprotein cholesterol (LDL-C), and apo-lipoprotein B (apo B) are associated with human atherosclerosis. Decreased levels of high density lipoprotein cholesterol (HDL-C) and its transport complex, apolipoprotein A (apo AI and apo AII) are associated with the development of atherosclerosis.

Fenofibrate is also effective in the treatment of Diabetes Type II and metabolic syndrome.

Fenofibrate is also indicated as adjunctive therapy to diet for treatment of adult patients with hypertriglyceridemia (Fredrickson Types IV and V hyperlipedemia). Improving glycemic control in diabetic patients showing fasting chylomicronemia will usually reduce fasting triglycerides and eliminate chylomicronemia and thereby obviating the need for pharmacologic intervention.

Fibrates are drug substances known to be are poorly and variably absorbed after oral administration. Normally they are prescribed to be taken with food in order to increase the bioavailability.

There have been a number of improvements in dosage form of the currently most used fibrate, fenofibrate, in an effort to increase the bioavailability of the drug and hence it's efficacy. However, there is still a need for improved dosage forms relative to the currently available compositions and dosage forms, which provide crystalline fenofibrate in micronized form. In particular, there remains a need for a composition and a dosage form exhibiting a suitable bioavailability, which substantially can reduce or overcome the differential between the bioavailability of the drug in patients who are fasted versus the bioavailability of the drug in patients who are fed, and/or which substantially can reduce or overcome the intra- and/or inter-individual variations observed with the current treatment with the available commercial products. Furthermore, there is also a need for novel dosage forms and/or compositions that enable reduction in observed side-effects.

Especially, there is an unmet need for developing a solid composition in particulate form in which the fibrate is in a dissolved state and that appears as a composition that is in the form of a powder, granules, granulates, particles, beads, pellets or other forms for particulate material and not in the form of a soft dosage form containing a liquid medium.

SUMMARY OF THE INVENTION

The inventors have now found that the bioavailabilty of fenofibrate can be significantly enhanced by dissolving a fibrate, for example fenofibrate, in a suitable vehicle and using the resulting composition for preparing a solid dosage form, i.e. a dosage form excluding material in liquid form. Fibrate, especially fenofibrate, is known to be insoluble in water, but the present invention provides pharmaceutical compositions and formulations exhibiting immediate release profiles which are comtemplated having significantly increased in vivo bioavailability in patients in need thereof. Especially, the inventors have succeeded in preparing a solid dosage form, such as a tablet, comprising the fibrate in dissolved form. The advantages of a solid and stable dosage form useful for oral administration are well-known.

Accordingly, in a first aspect the present invention relates to a solid oral dosage form comprising a fibrate dissolved in a vehicle, which is hydrophobic, hydrophilic or water-miscible. Useful solid dosage forms are in the form of tablets, beads, capsules, grains, pills, granulates, granules, powder, pellets, sachets or troches, and useful fibrates are, fenofibrate, bezafibrate, clofibrate, ciprofibrate and active metabolites and analogues thereof including any relevant fibric acid such as fenofibric acid.

In a second aspect, the invention relates to a pharmaceutical composition comprising a fibrate dissolved in a vehicle, which is hydrophobic, hydrophilic or water-miscible; and in a further aspect, the invention relates to a solid pharmaceutical composition in particulate form comprising a fibrate, a hydrophobic or a hydrophilic or water-miscible vehicle and an oil-sorption material, which composition exhibits an oil threshold value of at least 10%.

In yet another aspect, the invention relates to a method of manufacturing the solid oral dosage form or the pharmaceutical composition of the invention.

Further aspects of the invention are evident from the following description. Comparison in vivo tests in dogs have shown, cf. the examples herein, that solid dosage forms and compositions of the invention exhibit significantly enhanced bioavailability of fenofibrate compared to commercially available solid dosage forms containing the same active ingredient, i.e. to Tricor® tablet and Lipanthyl® capsules.

Further, it is strongly believed that the present invention provides solid dosage forms and/or compositions of fibrate capable of significantly reducing the intra- and/or inter-individual variation normally observed after oral administration. Furthermore, compositions and/or dosage forms according to the invention provide for a significant reduced food effect, i.e. the absorption is relatively independent on whether the patient takes the composition or dosage form together with or without any meal. It is contemplated that a modified release of the fibrate may reduce the number of gastrointestinal related side effects. Furthermore, it is contemplated that a significantly larger amount of the fibrate is absorbed and, accordingly, an equally less amount is excreted unchanged via feces.

DETAILED DESCRIPTION

Definitions

As used herein, the term "active ingredient" or "active pharmaceutical ingredient" means any component that is intended to furnish pharmacological activity or other direct effect in the diagnosis, cure, mitigation, treatment, or prevention of disease, or to affect the structure or any function of the body of man or other animals. The term includes those components that may undergo chemical change in the manufacture of the drug product and are present in the drug product in a modified form intended to furnish the specified activity or effect.

In the present context, the term "hydrophilic" describes that something 'likes water', i.e. a hydrophilic molecule or portion of a molecule is one that typically is electrically polarized and capable of forming hydrogen bonds with water molecules, enabling it dissolve more readily in water than in oil or other "non-polar" solvents.

In the present context, the term "amphiphilic" describes a molecule (as a surfactant) having a polar water-soluble group attached to a water-insoluble hydrocarbon chain. Thus, one end of the molecule is hydrophilic (polar) and the other is hydrophobic (non-polar).

In the present context, the term "hydrophobic" denotes a compound tending to be electrically neutral and non-polar, and thus preferring other neutral and nonpolar solvents or molecular environments.

As used herein, the term "water-miscible" denotes a compound being fully or partly miscible with water. For example, certain polar lipids are partly water-miscible.

As used herein, the term "vehicle" means any solvent or carrier in a pharmaceutical product that has no pharmacological role. For example, water is the vehicle for xilocalne and propylene glycol is the vehicle for many antibiotics.

In the present context, the term "solid dispersion" denotes a drug or active ingredient or substance dispersed on a particulate level in an inert vehicle, carrier, diluent or matrix in the solid state, i.e. usually a fine particulate dispersion.

In the present context, the term "solid solution" denotes a drug or active ingredient or substance dissolved on a molecular level in an inert vehicle, carrier, diluent or matrix in the solid state.

As used herein, the term "analogue" means a chemical compound that is structurally similar to another.

The term "drug" means a compound intended for use in diagnosis, cure, mitigation, treatment, or prevention of disease in man or other animals.

In this context, the term "dosage form" means the form in which the drug is delivered to the patient. This could be parenteral, topical, tablet, oral (liquid or dissolved powder), suppository, inhalation, transdermal, etc.

As used herein, the term "bioavailability" denotes the degree means to which a drug or other substance becomes available to the target tissue after administration.

As used herein, the term "bioequivalency" denotes a scientific basis on which generic and brand name drugs are compared with one another. For example, drugs are bioequivalent if they enter circulation at the same rate when given in similar doses under similar conditions. Parameters often used in bioequivalence studies are $t_{max}$, $C_{max}$, $AUC_{0\text{-}infinity}$, $AUC_{0\text{-}t}$. Other relevant parameters may be $W_{50}$, $W_{75}$ and/or MRT. Accordingly, at least one of these parameters may be applied when determining whether bioequivalence is present. Furthermore, in the present context, two compositions are regarded as bioequivalent if the value of the parameter used is within 80-125% of that of Prograf® or a similar commercially available tacrolimus-containing product used in the test.

In the present context "$t_{max}$" denotes the time to reach the maximal plasma concentration ($c_{max}$) after administration; $AUC_{0\text{-}infinity}$ or AUC denotes the area under the plasma concentration versus time curve from time 0 to infinity; $AUC_{0\text{-}t}$ denotes the area under the plasma concentration versus time curve from time 0 to time t; $W_{50}$ denotes the time where the plasma concentration is 50% or more of $C_{max}$; —$W_{75}$ denotes the time where the plasma concentration is 75% or more of $C_{max}$; and MRT denotes mean residence time for a fibrate such as fenofibrate (and/or an analogue thereof).

In this context, the term "medicine" means a compound used to treat disease, injury or pain. Medicine is justly distributed into "prophylactic," i.e. the art of preserving health, and "therapeutic", i.e. the art of restoring health.

In the present context, the terms "controlled release" and "modified release" are intended to be equivalent terms covering any type of release of tacrolimus from a composition of the invention that is appropriate to obtain a specific therapeutic or prophylactic response after administration to a subject. A person skilled in the art knows how controlled release/modified release differs from the release of plain tablets or capsules. The terms "release in a controlled manner" or "release in a modified manner" have the same meaning as stated above. The terms include slow release (that results in a lower $C_{max}$ and later $t_{max}$, but $t_{1/2}$ is unchanged), extended release (that results in a lower $C_{max}$, later $t_{max}$, but apparent $t_{1/2}$ is longer); delayed release (that result in an unchanged $C_{max}$, but lag time and, accordingly, $t_{max}$ is delayed, and $t_{1/2}$ is unchanged) as well as pulsatile release, burst release, sustained release, prolonged release, chrono-optimized release, fast release (to obtain an enhanced onset of action) etc. Included in the terms is also e.g. utilization of specific conditions within the body e.g. different enzymes or pH changes in order to control the release of the drug substance.

In this context, the term "erosion" or "eroding" means a gradual breakdown of the surface of a material or structure, for example of a tablet or the coating of a tablet.

The Active Drug Substance

The drug or active substance of the dosage forms and pharmaceutical compositions of this invention is a fibrate. Examples of useful fibrates are bezafibrate, ciprofibrate, clinofibrate, clofibrate, etofylline, clofibrate, fenofibrate, gemfibrozil, pirifibrate, simfibrate and tocofibrate; particularly useful are gemfibrozil, fenofibrate, bezafibrate, clofibrate, ciprofibrate and active metabolites and analogues thereof including any relevant fibric acid such as fenofibric acid. In a preferred embodiment, the fibrate is fenofibrate or an analogue thereof. However, the dosage forms and compositions of the invention may also comprise a mixture of two, three or even four different fibrates and/or fibric acids.

The concentration of fibrate in the vehicle is at least 10% w/w, based on the total weight of the fibrate and the vehicle; preferably at least 15% w/w, or at least 16% w/w, or at least 17% w/w, or at least 20% w/w, or at least 25% w/w, or at least 30% w/w, especially at least 35% w/w, based on the total weight of the fibrate and the vehicle; and the concentration of fibrate in the vehicle is at the most 90% w/w, based on the total weight of the fibrate and the vehicle, or at the most 80% w/w, or at the most 75% w/w, or at the most 70% w/w, or at the most 60% w/w, or at the most 50% w/w, or at the most 40% w/w, or not above 35% w/w, based on the total weight of the fibrate and the vehicle. Preferably, the fibrate is fully dissolved in the non-aqueous vehicle. However, a minor occurrence of crystalline or microcrystalline active drug may not influence on the enhanced bioavailability of the solid dosage forms and pharmaceutical compositions of the invention. Accordingly, at least 90% w/w of the fenofibrate is dissolved in the vehicle, preferably is at least 93% w/w, or at least 95% w/w, or at least 97% w/w, or at least 98% w/w, or at least 99% w/w, or at least 99.5% w/w, or at least 99.9% w/w, of the fenofibrate present in the dosage form or the pharmaceutical compostion fully dissolved in the vehicle or the vehicle system.

In addition to the content of fibrate, the dosage forms and pharmaceutical compositions of the invention may comprise further active drug substances, preferably one additional drug substances. Preferably, such an additional drug substance is of a type normally employed for the same indications as fibrate. A specific example is ezetimibe. However, combination products with three or even four drug substances used for the same indication are contemplated as well as combination products comprising two, three or four active ingredients for different indications or therapies.

Examples of additional drug substances are other antilipidemic agents like statins; lipid regulators like: acipimox, binifibrate, etofibrate, niceritrol, nicofibrate, pirozadil, ronifibrate, tocoferil nicotinate; combination with cardiovascular drugs like ace inhibitors: alacepril, benazepril, captopril, cilazapril, delapril, enalapril, enalaprilat, fosinopril, imidapril, lisinopril, moexipril, perindopril, quinapril, ramipril, spirapril, temocapril, teprotide, trandolapril, zofenopril; calcium channel blockers like: amlodipine, aranidipine, azelnidipine, barnidipine, benidipine, bepridil, cilnidipine, diltiazem, efonidipine, felodipine, gallopamil, isradipine, lacidipine, lercanidipine, manidipine, mibefradil, nicardipine, nifedipine, nilvadipine, nimodipine, nisoldipine, nitrendipine, verapamil; alpha-blockers like: alfuzosin, bunazosin, doxazosin, indoramin, naftopidil, phenoxybenzamine, phentolamine, prazosin, tamsulosin, terazosin, thymoxamine, tolazoline, urapidil; beta-blockers like: acebutolol, aiprenolol, amosulalol, arotinolol, atenolol, befunolol, betaxolol, bevantolol, bisoprolol, bopindolol, bucindolol, bunitrolol, bupranolol, carazolol, carteolol, carvedilol, celiprolol, esmolol, indenolol, labetalol, landiolol, levobetaxolol, levobunolol, mepindolol, metipranolol, metoprolol, nadolol, nebivolol, nipradilol, oxprenolol, penbutolol, pindolol, propranolol, sotalol, talinolol, tertatolol, timolol; angiotensin ii blockers like: candesartan, eprosartan, irbesartan, losartan, olmesartan, tasosartan, ref. telmisartan, valsartan; vasodilators like: cadralazine, diazoxide, dihydralazine, endralazine, hydralazine, minoxidil, todralazine, tolazoline, carbocromen, cinepazet, ref. cloridarol, dilazep, etafenone, fendiline, hexobendine, oxyfedrine, trapidil, trimetazidine, azapetine, bamethan, bencyclane, buflomedil, butalamine, calcitonin gene-related peptide, cetiedil, cinepazide, cyclandelate, di-isopropylammonium ichloroacetate, fasudil, ifenprodil, inositol nicotinate, naftidrofuryl, nicotinyl alcohol, oxpentifylline [pentoxifylline], pentifylline, pipratecol, propentofylline, raubasine, xantinol icotinat; centrally acting hypertensives: apraclonidine, brimonidine, clonidine, guanabenz, guanfacine, methyldopa, moxonidine, rilmenidine, tiamenidine; anti arrhythmic drugs like: ajmaline, cibenzoline, disopyramide, hydroquinidine, pirmenol, procainamide, quinidine, aprindine, mexiletine, tocamide, diprafenone, encamide, flecamide, lorcamide, pilsicamide, propafenone, bretylium, acecamide, amiodarone, azimilide, bretylium, cibenzoline, dofetilide, ibutilide, nifekalant, sotalol, cibenzoline, verapamil; anti platelets like: abciximab, aspirin, cilostazol, clopidogrel, cloricromen, dipyridamole, ditazole, eptifibatide, indobufen, lamifiban, orbofiban, picotamide, sarpogrelate, sibrafiban, ticlopidine, tirofiban, trapidil, triflusal, xemilofiban; diuretics like: acetazolamide, brinzolamide, diclofenamide, dorzolamide, methazolamide, azosemide, bumetanide, etacrynic acid, etozolin, frusemide, piretanide, torasemide, isosorbide, mannitol, amiloride, canrenone, potassium canrenoate, spironolactone, triamterene, altizide, bemetizide, bendrofluazide, benzthiazide, butizide, chlorothiazide, chlortalidone, clopamide, cyclopenthiazide, cyclothiazide, epitizide, hydrochlorothiazide, hydroflumethiazide, indapamide, mebutizide, mefruside, methyclothiazide, meticrane, metolazone, polythiazide, quinethazone, teclothiazide, trichlormethiazide, tripamide, xipamide; antidiabetic drugs like: acarbose acetohexamide biguanide antidiabetics buformin carbutamide chlorpropamide epalrestat glibenclamide glibornuride gliclazide glimepiride glipizide gliquidone glisentide glisolamide glisoxepide glybuzole glyclopyramide glycyclamide glymidine sodium metformin hydrochloride midaglizole miglitol nateglinide phenformin hydrochloride pimagedine pioglitazone hydrochloride pramlintide repaglinide rosiglitazone sorbinil tolazamide tolbutamide troglitazone voglibose substances like: q10, vitamins (nicotinamid, pyridoxine hcl, b12, tocopheroles, ascorbic acids, and others), and antioxidants in general are also included in the useful combinations.

The additional drug substance or substances may also be included in or used in combination with drugs that may lead to an undesired level of triglycerides and/or cholesterol. Thus, a composition according to the invention may be included in or used in combination with drugs like e.g. isotretinoin or a retroviral protease inhibitor like HIV protease inhibitors, with an antipsychotic like olanzapine and others.

As mentioned, combination products with fibrates are not limited to combinations of two active substances, triple or quadruple therapies could also be of particular interest.

The Vehicle

Vehicles useful in the present context are vehicles, which are water-miscible, hydrophilic or hydrophobic. Useful vehicles are non-aqueous substances.

Examples of hydrophobic vehicles useful in the present invention are straight chain saturated hydrocarbons, paraffins; fats and oils such as cacao butter, beef tallow, lard; higher fatty acid such as stearic acid, myristic acid, palmitic acid; hydrogenated tallow, substituted and/or unsubstituted triglycerides, yellow beeswax, white beeswax, carnauba wax, castor wax, japan wax, and mixtures thereof.

Examples of water-miscible vehicles useful in the present invention are water-miscible polar lipids such as sorbitan esters, polyether glycol esters; higher alcohols such as cetanol, stearyl alcohol; glyceryl monooleate, substituted and/or unsubstituted monoglycerides, substituted and/or unsubstituted diglycerides, and mixtures thereof. In a more preferred embodiment, the vehicle is hydrophilic or water-miscible. Preferably, the vehicle is selected from the group consisting of polyethylene glycols, polyoxyethylene oxides, poloxamers, polyoxyethylene stearates, poly-epsilon caprolactone and mixtures thereof. However, the vehicle may advantageously also be a polyglycolized glyceride such as one of the numerous products sold under the registered trade mark Gelucire®, for example Gelucire 44/14.

Examples of useful hydrophilic or water-miscible vehicles are polyvinylpyrrolidones, polyvinyl-polyvinylacetate copolymers (PVP-PVA), polyvinyl alcohol (PVA), PVP polymers, acrylic polymers, polymethacrylic polymers (Eudragit RS; Eudragit RL, Eudragit NE, Eudragit E), myristyl alcohol, cellulose derivatives including hydroxypropyl methylcellulose (HPMC), hydroxypropyl cellulose (HPC), methylcellulose, sodium carboxy-methylcellulose, hydroxyethyl cellulose, pectins, cyclodextrins, galactomannans, alginates, carragenates, xanthan gums and mixtures thereof.

The vehicle is preferably a mixture of two or more substances.

The vehicle may also be an oily material as defined and described below.

Preferably, the melting point of the vehicle is preferably in the range of 10° C. to 250° C., preferably in the range of 30° C. to 100° C., more preferably in the range of 40° C. to 75° C., especially in the range of 40° C. to 70° C.

In a preferred embodiment of the invention, the vehicle is polyethylene glycol (PEG), preferably having an average molecular weight of at least 3000, more preferably at least 4000, optionally in admixture with a poloxamer such as e.g. poloxamer 188, in a preferred weight ratio of between 1:3 and 10:1, preferably between 1:1 and 5:1, more preferably between and 3:2 4:1, especially between 2:1 and 3:1, in particular about 7:3.

Bioavailability

In general, it is known that the absorption and bioavailability of a therapeuticcally active substance can be affected by a variety of factors when administered orally. Such factors include the presence of food in the gastrointestinal tract and, in general, the gastric residence time of a drug substance is significantly longer in the presence of food than in the fasted state. If the bioavailability of a drug substance is affected beyond a certain point due to the presence of food in the gastrointestinal tract, the drug substance is said to exhibit a food effect. Food effects are important because there is a risk associated with administering the drug substance to a patient who has eaten recently. The risk derives from the potential that absorption into the bloodstream may be adversely affected to the point that the patient risks insufficient absorption to remedy the condition for which the drug was administered. In the case of e.g. fenofibrate the situation is different in that food increases the uptake. Thus, lack of intake of food simultaneously with the drug substances may lead to insufficient absorption. The extent of absorption of a commercially available product Tricor® containing fenofibrate (from Abbott) is increased by approximately 35% under fed as compared to fasting conditions.

As described above, there remains a need for new pharmaceutical compositions comprising one or more fibrates exhibiting, suitable bioavailability of the active compound and/or reduced or eliminated food effect. In the present context, the term "suitable bioavailability" is intended to mean that administration of a composition according to the invention will result in a bioavailability that is improved compared to the bioavailability obtained after administration of the active substance(s) in a plain tablet; or the bioavailability is at least the same or improved compared to the bioavailability obtained after administration of a commercially available product containing the same active substance(s) in the same amounts. In particular it is desired to obtain more complete uptake of the active compound, and thereby provide for a possible reduction of the administered dosages. Further, pharmaceutical compositions and dosage forms comprising a fibrate may also reduce or negate the need for food to be takes simultaneously with the dosage form thereby allowing patients more freedom on when the drug is taken. Also, improved or enhanced bioavailability will lead to an improved treatment because it will be possible to obtain the same therapeutic response with a decreased dose and/or a less frequent administration and less variability in plasma levels and no food restrictions. Another way of obtaining an improved treatment of conditions where e.g. fenofibrate is indicated is by balancing the release of fenofibrate to the gastrointestinal tract in such a manner that an enhanced plasma concentration of fenofibrate is obtained initially or delayed with respect to the time of administration, i.e. by applying modified or delayed release compositions containing one or more fibrates.

In one embodiment, the invention relates to a pharmaceutical composition in particulate form or solid dosage form comprising one or more fibrates, wherein the composition upon oral administration to a mammal in need thereof exhibits an $AUC/AUC_{control}$ value of at least about 1.0, the $AUC_{control}$ being determined using a commercially available product containing the same fibrate, and the AUC values being determined under similar conditions.

No absolute bioavailability data based on an injectable composition are available e.g. for fenofibrate (most likely due to solubility problems in aqueous media). The commercially available compositions containing fenofibrate include surface-active agents and/or e.g. a lipophilic medium. The surface-active agents may impart improved bioavailability and therefore, the bioavailability of such a composition may be sufficient already. However, there is still a need for developing a flexible formulation technique that enables preparation of a variety of dosage forms. Accordingly, the requirement to such improved and/or more flexible compositions may be to obtain the same or better bioavailability than already seen from the commercially available products.

Accordingly, in further embodiments of the invention, the $AUC/AUC_{Control}$ value obtained by administering the solid dosage form or pharmaceutical composition of the invention is at least about 1.1 such as, e.g., at least about 1.2, at least about 1.3, at least about 1.4, at least about 1.5, about 1.75 or more, about 1.8 or more, about 1.9 or more, about 2.0 or more, about 2.5 or more, about 2.75 or more, about 3.0 or more, about 3.25 or more, about 3.5 or more, about 3.75 or more, about 4.0 or more, about 4.25 or more, about 4.5 or more, about 4.75 or more or about 5.0 or more, the AUC values being determined under similar conditions.

Likewise, the $c_{max}$ value obtained by administering the solid dosage form or pharmaceutical composition of the invention relative to the $c_{max}$ value of commercially available Tricor® tablets is at least about 1.1, or at least about 1.2, or at least about 1.3, or at least about 1.4, or at least about 1.5, or at least about 1.6 or more, or at least about 2.0, or at least about 2.5, or at least about 3.0, the $c_{max}$ values being determined under similar conditions.

Another object of the invention is to reduce or eliminate the food effect.

Thus, in another aspect, the invention relates to a pharmaceutical composition in particulate form or solid dosage form comprising one or more fibrates, wherein the composition or solid dosage form upon oral administration to a mammal in need thereof does not exhibit a significant adverse food effect as evidenced by a value of ($AUC_{fed}/AUC_{fasted}$) of at least about 0.85 with a lower 90% confidence limit of at least 0.75. In a specific embodiment, the pharmaceutical composition or solid dosage form of the invention has a value of ($AUC_{fed}/AUC_{fasted}$) that is about 0.9 or more such as, e.g., about 0.95 or more, about 0.97 or more or about 1 or more.

In other words, the difference between a bioequivalence parameter measured after oral administration to a mammal with and without food, respectively, is less than 25% such as, e.g., less than 20%, less than 15%, less than 10% or less than 5%.

In another aspect, the invention relates to a pharmaceutical composition in particulate form or solid dosage form comprising a fibrate, wherein the composition upon oral administration to a mammal in need thereof is essentially bioequivalent with a commercially available product containing the same fibrate when administered in the same or lower dose as the commercially available product containing the same fibrate. In specific embodiments thereof, the dose is at the most about 98% w/w such as, e.g., at the most about 95% w/w, at the most about 90% w/w, at the most about 85% w/w, at the most about 80% w/w, at the most about 75% w/w, at the most about 70% w/w, at the most about 65% w/w, at the most about 60% w/w, at the most about 55% w/w or at the most about 50% w/w of the dose of the fibrate administered in the form of a commercially available product containing the same fibrate.

Normally, the bioequivalence is determined by means of at least one of the following parameters: $t_{max}$ (time to reach maximal plasma concentration), $c_{max}$ (maximal plasma concentration), $AUC_{0-t}$ (area under the curve from time 0 to time t), $AUC_{0\text{-}infinity}$ (area under the curve from time 0 to time infinity), $W_{50}$ (time period where the plasma concentration is 50% or more of $c_{max}$), $W_{75}$ ((time period where the plasma concentration is 75% or more of $c_{max}$) and/or MRT (mean residence time).

A major problem with treatment with a fibrate is the large intra- or inter-individual variation. Thus, in a further aspect the invention relates to a pharmaceutical composition in particulate form comprising one or more fibrates, wherein the composition upon oral administration to a mammal in need thereof reduces inter- and/or intra-individual variations compared to those of a commercially available product containing the same fibrate under the same conditions and in a dose that provides an equivalent therapeutic effect.

In the comparison tests mentioned above, the commercially available product is Tricor® in the form of tablets or, alternatively, Tricor® in the form of capsules, when the fibrate is fenofibrate. When the fibrate is gemfibrozil then a suitable commercially available product is Lopid®; when the fibrate is bezafibrate a suitable commercially available product is Bezalip®; when the fibrate is clofibrate then a suitable commercially available product is Atromid®; and when the fibrate is ciprofibrate then a suitable commercially available product is Lipanon®.

A convenient method for determining whether a suitable amount of a fibrate has been absorbed may be to determine the content of unchanged fibrate excreted via the feces. Thus, in one embodiment the invention relates to a solid pharmaceutical composition or solid dosage form, wherein at most about 25% w/w such as, e.g., at the most about 20% w/w, at the most about 15% w/w, at the most about 10% w/w, at the most about 5% w/w of the fibrate contained in the composition is excreted in the feces after oral administration.

Method of Manufacture

The particulate composition of the invention may be prepared by any method which is suitable for incorporation of poorly water-soluble active substances. The pharmaceutical compositions may be prepared by any convenient method such as, e.g. granulation, mixing, spray drying etc. A particularly useful method is the method disclosed in the international application published as WO 03/004001, which describes a process for preparation of particulate material by a controlled agglomeration method, i.e. a method, which enables a controlled growth in particle size. The method involves spraying a first composition comprising the active substance and a vehicle in liquid form onto a solid carrier. Normally, the vehicle has a melting point of at least 5° C., but the melting point must indeed be below the melting point of the active substance. In the present invention, the melting point of the vehicle and should not exceed 250° C.

It is within the skills of the average practioner to select a suitable vehicle being pharmaceutical acceptable, capable of dispersing or fully or at least partly dissolving the active substance and having a melting point in the desired range using general knowledge and routine experimentation. Suitable candidate for carriers are described in WO 03/004001, which is herein incorporated by reference.

In the present context, suitable vehicles are e.g. those mentioned as vehicles or as oily materials as well as those disclosed in WO 03/004001. An advantage of using the controlled agglomeration method described in WO 03/004001 is that it is possible to apply a relatively large amount of a liquid system to a particulate material without having an undesirable growth in particle size. Accordingly, in one embodiment of the invention, the particulate material of a pharmaceutical composition has a geometric weight mean diameter $d_{gw}$ of $\geq 10$ μm such as, e.g. $\geq 20$ μm, from about 20 to about 2000, from about 30 to about 2000, from about 50 to about 2000, from about 60 to about 2000, from about 75 to about 2000 such as, e.g. from about 100 to about 1500 μm, from about 100 to about 1000 μm or from about 100 to about 700 μm, or at the most about 400 μm or at the most 300 μm such as, e.g., from about 50 to about 400 μm such as, e.g., from about 50 to about 350 μm, from about 50 to about 300 μm, from about 50 to about 250 μm or from about 100 to about 300 μm.

The compositions and dosage forms of the invention are preferably formed by spray drying techniques, controlled agglomeration, freeze-drying or coating on carrier particles or any other solvent removal process. The dried product contains the active substance present preferably in dissolved form either fully dissolved as a solid solution or partly dissolved as a solid dispersion including a molecular dispersion and a solid solution.

However, the composition and dosage forms of the invention are preferably manufactured by a method comprising the steps of:

i) bringing the vehicle in liquid form, i.e. melting the vehicle if solid at room temperature,
ii) maintaining the liquid vehicle at a temperature below the melting point of the fibrate,
iii) dissolving the desired amount of fibrate in the vehicle,
iv) spraying the resulting solution onto a solid carrier having a temperature below the melting point of the vehicle,
v) mechanically working the resulting composition to obtain particles, i.e. a particulate material, and
vi) optionally subjecting the particulate material to conventional methods for preparing solid dosage forms.

The pharmaceutical compositions comprising the active substance at least partly in form of a solid dispersion or solution may in principle be prepared using any suitable procedure for preparing pharmaceutical compositions known within the art. A solid dispersion may be obtained in different ways e.g. by employing organic solvents or by dispersing or dissolving the active substance in another suitable medium (e.g. an oily material that is in liquid form at room temperature or at elevated temperatures). Solid dispersions (solvent method) are prepared by dissolving a physical mixture of the active substance (e.g. a drug substance) and the carrier in a common organic solvent, followed by evaporation of the solvent. The carrier is often a hydrophilic polymer. Suitable organic solvents include pharmaceutical acceptable solvent in which the active substance is soluble such as methanol, ethanol, methylene chloride, chloroform, ethylacetate, acetone or mixtures thereof.

Suitable water-soluble carriers include polymers such as polyethylene glycol, poloxamers, polyoxyethylene stearates, poly-epsilon-caprolactone, polyvinylpyrrolidone (PVP), polyvinylpyrrolidone-polyvinylacetate copolymer PVP-PVA (Kollidon VA64), poly-methacrylic polymers (Eudragit RS, Eudragit RL, Eudragit NE, Eudragit E) and polyvinyl alcohol (PVA), hydroxypropyl cellulose (HPC), hydroxypropyl methyl cellulose (HPMC), methyl cellulose, and poly (ethylene oxide) (PEO).

Polymers containing acidic functional groups may be suitable for solid dispersions, which release the active substance in a preferred pH range providing acceptable absorption in the intestines. Such polymers may be one or more selected from the group comprising hydroxypropyl methylcellulose phtalate (HMPCP), polyvinyl acetate phtalate (PVAP), hydroxypropylmethylcellulose acetate succinate (HPMCAS), alginate, carbomer, carboxymethylcellulose, methacrylic acid copolymer (Eudragit L, Eudragit S), shellac, cellulose acetate phthalate (CAP), starch glycolate, polacrylin, methyl cellulose acetate phtalate, hydroxypropyulcellulose acetate phthalate, cellulose acetate terephtahalate, cellulose acetate isophthalate and cellulose acetate trimellitate.

The weight ratio of active substance to polymer may be in a range of from about 3:1 to about 1:20. However, narrower ranges of from about 3:1 to about 1:5, such as, e.g., from about 1:1 to about 1:3 or about may also be used.

Apart from using the organic solvent based method, solid dispersion or solid solutions of one or more fibrates may be also obtained by dispersing and/or dissolving the active compound in the carrier composition used in the controlled agglomeration method. Stabilizing agents etc. may be added in order to ensure the stability of the solid dispersion/solution.

Pharmaceutical Excipients and Additives

In the present context the terms "pharmaceutically acceptable excipient" are intended to denote any material, which is inert in the sense that it substantially does not have any therapeutic and/or prophylactic effect per se. Such excipient(s) may be added with the purpose of making it possible to obtain a pharmaceutical, cosmetic and/or foodstuff composition, which have acceptable technical properties.

Examples of suitable excipients for use in a composition or solid dosage form according to the invention include fillers, diluents, glidants, disintegrants, binders, lubricants etc. or mixture thereof. As the composition or solid dosage form according to the invention may be used for different purposes, the choice of excipients is normally made taken such different uses into considerations. Other pharmaceutically acceptable excipients for suitable use are e.g. acidifying agents, alkalizing agents, preservatives, antioxidants, buffering agents, chelating agents, coloring agents, complexing agents, emulsifying and/or solubilizing agents, flavors and perfumes, humectants, sweetening agents, wetting agents etc.

Examples of suitable fillers, diluents and/or binders include lactose (e.g. spray-dried lactose, α-lactose, β-lactose, Tabletose®, various grades of Pharmatose®, Microtose® or Fast-Floc®), microcrystalline cellulose (various grades of Avicel®, Elcema®, Vivacel®, Ming Tai® or Solka-Floc®), hydroxypropylcellulose, L-hydroxypropylcellulose (low substituted), hydroxypropyl methylcellulose (HPMC) (e.g. Methocel E, F and K, Metolose SH of Shin-Etsu, Ltd, such as, e.g. the 4,000 cps grades of Methocel E and Metolose 60 SH, the 4,000 cps grades of Methocel F and Metolose 65 SH, the 4,000, 15,000 and 100,000 cps grades of Methocel K; and the 4,000, 15,000, 39,000 and 100,000 grades of Metolose 90 SH), methylcellulose polymers (such as, e.g., Methocel A, Methocel A4C, Methocel A15C, Methocel A4M), hydroxyethylcellulose, sodium carboxymethylcellulose, carboxymethylene, carboxymethylhydroxyethylcellulose and other cellulose derivatives, sucrose, agarose, sorbitol, mannitol, dextrins, maltodextrins, starches or modified starches (including potato starch, maize starch and rice starch), calcium phosphate (e.g. basic calcium phosphate, calcium hydrogen phosphate, dicalcium phosphate hydrate), calcium sulfate, calcium carbonate, sodium alginate, collagen etc.

Specific examples of diluents are e.g. calcium carbonate, dibasic calcium phosphate, tribasic calcium phosphate, calcium sulfate, microcrystalline cellulose, powdered cellulose, dextrans, dextrin, dextrose, fructose, kaolin, lactose, mannitol, sorbitol, starch, pregelatinized starch, sucrose, sugar etc.

Specific examples of disintegrants are e.g. alginic acid or alginates, microcrystalline cellulose, hydroxypropyl cellulose and other cellulose derivatives, croscarmellose sodium, crospovidone, polacrillin potassium, sodium starch glycolate, starch, pregelatinized starch, carboxymethyl starch (e.g. Primogel® and Explotab®) etc. Specific examples of binders are e.g. acacia, alginic acid, agar, calcium carrageenan, sodium carboxymethylcellulose, microcrystalline cellulose, dextrin, ethylcellulose, gelatin, liquid glucose, guar gum, hydroxypropyl methylcellulose, methylcellulose, pectin, PEG, povidone, pregelatinized starch etc.

Glidants and lubricants may also be included in the second composition. Examples include stearic acid, magnesium stearate, calcium stearate or other metallic stearate, talc, waxes and glycerides, light mineral oil, PEG, glyceryl behenate, colloidal silica, hydrogenated vegetable oils, corn starch, sodium stearyl fumarate, polyethylene glycols, alkyl sulfates, sodium benzoate, sodium acetate etc.

Other excipients which may be included in a composition or solid dosage form of the invention are e.g. flavoring agents, coloring agents, taste-masking agents, pH-adjusting agents, buffering agents, preservatives, stabilizing agents, anti-oxidants, wetting agents, humidity-adjusting agents, surface-active agents, suspending agents, absorption enhancing agents, agents for modified release etc.

Other additives in a composition or a solid dosage form according to the invention may be antioxidants like e.g. ascorbic acid, ascorbyl palmitate, butylated hydroxyanisole, butylated hydroxytoluene, hypophosphorous acid, monothioglycerol, potassium metabisulfite, propyl gallate, sodium formaldehylde sulfoxylate, sodium metabisulfite, sodium thiosulfate, sulfur dioxide, tocopherol, tocopherol acetate, tocopherol hemisuccinate, TPGS or other tocopherol derivatives, etc. The carrier composition may also contain e.g. stabilising agents. The concentration of an antioxidant and/or a stabilizing agent in the carrier composition is normally from about 0.1% w/w to about 5% w/w.

A composition or solid dosage form according to the invention may also include one or more surfactants or substances having surface-active properties. It is contemplated that such substances are involved in the wetting of the slightly soluble active substance and thus, contributes to improved solubility characteristics of the active substance. Suitable surfactans for use in a composition or a solid dosage form according to the invention are surfactants such as, e.g., hydrophobic and/or hydrophilic surfactants such as those disclosed in WO 00/50007 in the name of Lipocine, Inc.

Specific examples of suitable surfactants are polyethoxylated fatty acids such as, e.g. fatty acid mono- or diesters of polyethylene glycol or mixtures thereof such as, e.g. mono- or diesters of polyethylene glycol with lauric acid, oleic acid, stearic acid, myristic acid, ricinoleic acid, and the polyethylene glycol may be selected from PEG 4, PEG 5, PEG 6, PEG 7, PEG 8, PEG 9, PEG 10, PEG 12, PEG 15, PEG 20, PEG 25, PEG 30, PEG 32, PEG 40, PEG 45, PEG 50, PEG 55, PEG 100, PEG 200, PEG 400, PEG 600, PEG 800, PEG 1000, PEG 2000, PEG 3000, PEG 4000, PEG 5000, PEG 6000, PEG 7000, PEG 8000, PEG 9000, PEG 1000, PEG 10,000, PEG 15,000, PEG 20,000, PEG 35,000, polyethylene glycol glycerol fatty acid esters, i.e. esters like the above-mentioned but in the form of glyceryl esters of the individual fatty acids; glycerol, propylene glycol, ethylene glycol, PEG or sorbitol esters with e.g. vegetable oils like e.g. hydrogenated castor oil, almond oil, palm kernel oil, castor oil, apricot kernel oil, olive oil, peanut oil, hydrogenated palm kernel oil and the like, polyglycerized fatty acids like e.g. polyglycerol stearate, polyglycerol oleate, polyglycerol ricinoleate, polyglycerol linoleate, propylene glycol fatty acid esters such as, e.g. propylene glycol monolaurate, propylene glycol ricinoleate and the like, mono- and diglycerides like e.g. glyceryl monooleate, glyceryl dioleae, glyceryl mono- and/or dioleate, glyceryl caprylate, glyceryl caprate etc.; sterol and sterol derivatives; polyethylene glycol sorbitan fatty acid esters (PEG-sorbitan fatty acid esters) such as esters of PEG with the various molecular weights indicated above, and the various Tween® series; polyethylene glycol alkyl ethers such as, e.g. PEG oleyl ether and PEG lauryl ether; sugar esters like e.g. sucrose monopalmitate and sucrose monolaurate; polyethylene glycol alkyl phenols like e.g. the Triton® X or N series; polyoxyethylene-polyoxypropylene block copolymers such as, e.g., the Pluronic® series, the Synperonic® series, Emkalyx®, Lutrol®, Supronic® etc. The generic term for these polymers is "poloxamers" and relevant examples in the present context are Poloxamer 105, 108, 122, 123, 124, 181, 182, 183, 184, 185, 188, 212, 215, 217, 231, 234, 235, 237, 238, 282, 284, 288, 331, 333, 334, 335, 338, 401, 402, 403 and 407; sorbitan fatty acid esters like the Span® series or Ariacel® series such as, e.g. sorbinan monolaurate, sorbitan monopalmitate, sorbitan monooleate, sorbitan monostearate etc.; lower alcohol fatty acid esters like e.g. oleate, isopropyl myristate, isopropyl palmitate etc.; ionic surfactants including cationic, anionic and zwitterionic surfactants such as, e.g. fatty acid salts, bile salts, phospholipids, phosphoric acid esters, carboxylates, sulfates and sulfonates etc.

When a surfactant or a mixture of surfactants is present in a composition or a solid dosage form of the invention, the concentration of the surfactant(s) is normally in a range of from about 0, 1-80% w/w such as, e.g., from about 0.1 to about 20% w/w, from about 0.1 to about 15% w/w, from about 0.5 to about 10% w/w, or alternatively, from about 0.10 to about 80% w/w such as, e.g. from about 10 to about 70% w/w, from about 20 to about 60% w/w or from about 30 to about 50% w/w.

In a specific aspect of the invention, the at least one of the one or more pharmaceutically acceptable excipients is selected from the group consisting of silica acid or a derivative or salt thereof including silicates, silicon dioxide and polymers thereof; magnesium aluminosilicate and/or magnesium aluminometasilicate, bentonite, kaolin, magnesium trisilicate, montmorillonite and/or saponite, Nuesellin™ Sorption Materials Materials such as those mentioned immediately above are especially useful as a sorption material for oily materials in pharmaceuticals, cosmetics and/or foodstuff. In a specific embodiment, the material is used as a sorption material for oily materials in pharmaceuticals. The material that has the ability to function as a sorption material for oily materials is also denoted "oil sorption material".

Furthermore, in the present context the term "sorption" is used to denote "absorption" as well as "adsorption". It should be understood that whenever one of the terms is used it is intended to cover the phenomenon absorption as well as adsorption. The terms "sorption material" and "oil sorption material" is intended to have the same meaning.

A sorption material suitable for use according to the present invention is a solid pharmaceutically acceptable material, which—when tested as described herein—
i) has an oil threshold value of 10% or more, when tested according to the Threshold Test disclosed herein, and which material is used in a composition of the invention further fulfilling one or both of i) and ii):
i) the compositon releases at least 30% of the hydrophobic or a hydrophilic or water-miscible vehicle, when tested according to the Release Test;
ii) the composition, in the form of a tablet, contains at least about 90% w/w of the oil-sorption material, and exhibits a disintegration time of at the most 60 minutes when tested according to the Ph. Eur. Disintegration Test.

The material is especially useful as a sorption material for oily materials in pharmaceuticals, cosmetics and/or foodstuff, especially in pharmaceuticals.

It is important that the oil sorption material fulfills at least two tests. One of the tests is mandatory, i.e. the Threshold Test must be met. This test gives a measure for how much oily material the oil sorption material is able to absorb while retaining suitable flowability properties. It is important that an oil sorption material for use according to the invention (with or without oil absorbed) has a suitable flowability so that it easily can be admixed with other excipients and/or further processed into compositions without significant problems relating to e.g. adherence to the apparatus involved. The test is described below in Materials and Methods and guidance is given for how the test is carried out. The Threshold Test involves the determination of the flowability of the solid material loaded with different amounts of oil.

From above it is seen that the oil threshold value normally must exceed 10% and often the oil sorption material has an oil threshold value of at least about 15%, such as, e.g., at least about 20%, at least about 25%, at least about 30%, at least about 35%, at least about 40%, or at least about 45%.

An especially suitable material for use according to the invention, Aeropearl 300, has a very high oil threshold value of about 60%. Accordingly, materials that have an oil threshold value of at least about 50%, such as, e.g., at least about 55% or at least about 60% are used in specific embodiments of the present invention.

Furthermore, an oil sorption material for use according to the invention must fulfill at least one further test, namely a release test and/or a disintegration test.

The release test gives a measure of the ability of an oil sorption material to release the oil that is absorbed to the material when contacted with water. This ability is very important especially in those situations where an active substance is contained in the oily material. If the oil sorption material is not capable of releasing the oil from the material then there is a major risk that the active substance will only to a minor degree be released from the material. Accordingly, it is envisaged that bioavailability problems relating to e.g. poor absorption etc. will occur in such situations.

The requirements for the release test are that the solid pharmaceutical acceptable material, when tested as described herein, releases at least about 30% such as, e.g., at least about 35%, at least about 40%, at least about 45%, at least about 50%, at least about 55% or at least about 60% of an oil. As it appears from the examples herein a suitable oil sorption material like Aeroperl 300 has a much higher release. Therefore, in a specific embodiment of the invention, the solid pharmaceutical acceptable material, when tested as described herein, releases at least about 65% such as, e.g., at least about 70%, at least about 75% or at least about 80% of an oil.

The disintegration test is not performed on the solid material in particulate form but on a tablet made of the solid material. A requirement with respect to disintegration is important in order to ensure that the solid material, when included in solid dosage forms, does not impart unwanted properties to the dosage form e.g. leading to unwanted properties with respect to dissolution and bioavailability of the active substance contained in the dosage form. For some of the materials suitable for use according to the invention it is possible to press tablets containing 100% w/w of the solid material itself. If this is the case, the test is carried out on such tablets. However, it is envisaged that there may be situations where it is rather difficult to prepare tablets from the solid material alone. In such cases it is possible to add pharmaceutically acceptable excipients normally used in the preparation of compressed tablets up to a concentration of 10% w/w or less. Examples of suitable pharmaceutically acceptable excipients include fillers, diluents, binders and lubricants. However, excipients, normally classified as disintegrants, should be avoided.

Accordingly, the solid pharmaceutical acceptable material for use according to invention, when tested as described herein, in the form of a tablet should have a disintegration time of at the most 1 hour, when tested according to Ph. Eur. Disintegration test, the tablet containing about 90% w/w or more, such as, e.g., about 92.5% w/w or more, about 95% w/w or more, about 97.5% w/w or more or about 100% of the pharmaceutically acceptable material.

In a further embodiment, the solid pharmaceutical acceptable material, when tested as described herein, in the form of a tablet has a disintegration time of at the most about 50 min, such as, e.g., at the most about 40 min, at the most about 30 min, at the most about 20 min, at the most about 10 min or at the most about 5 min, when tested according to Ph. Eur. Disintegration test, the tablet containing about 90% w/w or more, such as, e.g., about 92.5% w/w or more, about 95% w/w or more, about 97.5% w/w or more or about 100% of the pharmaceutically acceptable material.

In a specific embodiment, the solid material used as a sorption material fulfils all three tests. Thus, the solid pharmaceutical acceptable material, when tested as described herein, i) has an oil threshold value of at least about 10%, such as, e.g., at least about 15%, at least about 20%, at least about 25%, at least about 30%, at least about 35%, at least about 40%, at least about 45%, at least about 50%, at least about 55% or at least about 60%, ii) releases at least about 30% such as, e.g., at least about 35%, at least about 40%, at least about 45%, at least about 50%, at least about 55%, at least about 60%, at least about 65%, at least about 70%, at least about 75% or at least about 80% of an oil, and iii) in the form of a tablet has a disintegration time of at the most 1 hour such as at the most about 50 min, at the most about 40 min, at the most about 30 min, at the most about 20 min, at the most about 10 min or at the most about 5 min, when tested according to Ph. Eur. Disintegration test, the tablet containing about 90% w/w or more, such as, e.g., about 92.5% w/w or more, about 95% w/w or more, about 97.5% w/w or more or about 100% of the pharmaceutically acceptable material.

Other specific embodiments of the invention are those, wherein the solid pharmaceutical material used as a sorption material in a composition according of the invention, when tested as described herein, i) has an oil threshold value of at least about 55%; the solid pharmaceutical material, when tested as described herein, ii) releases at least about 75% of an oil; and/or the solid pharmaceutical material, when tested as described herein, iii) in the form of a tablet has disintegration time of at the most about 10 min, when tested according to Ph. Eur. Disintegration test, the tablet containing about 97.5% w/w of the pharmaceutically acceptable material.

The solid pharmaceutically acceptable material used as a sorption material in a composition according to the invention is normally a particulate material in the form of e.g. powders, particles, granules, granulates etc.

Such particulate material suitable for use as an oil sorption material has normally a bulk density of about 0.15 g/cm$^3$ or more such as, e.g., at least about 0.20 g/cm$^3$ or at least about 0.25 g/cm$^3$.

Furthermore, the oil sorption material normally has an oil absorption value of at least about 100 g oil/100 g such as, e.g., at least about 150 g oil/100 g, at least about 200 g oil/100 g, at least about 250 g oil/100 g, at least about 300 g oil/100 g or at least about 400 g oil/100 g pharmaceutically acceptable material. The oil absorption value is determined as described in the experimental section herein.

The present inventors have found that a common feature of some of the materials suitable for use as oil sorption material is that they have a relatively large surface area. Accordingly, pharmaceutically acceptable material for use as an oil sorption material according to the invention may have a BET surface area of at least 5 m$^2$/g such as, e.g., at least about 25 m$^2$/g, at least about 50 m$^2$/g, at least about 100 m$^2$/g, at least about 150 m$^2$/g, at least about 200 m$^2$/g, at least about 250 m$^2$/g or at least about 275 m$^2$/g.

As mentioned above one of the characteristic features of a pharmaceutically acceptable material for use as an oil sorption material according to the invention is that it retains a good flowability even if it has been loaded with oily material. Thus, the flowability of the pharmaceutically acceptable material loaded with 25% w/w or more such as, e.g. 30% w/w or more, 40% w/w or more, 45% w/w or more, 50% w/w or more, 55% w/w or more, 60% w/w or more, 65% w/w or more or about 70% w/w viscoleo will normally meet the Ph. Eur. requirements. Notably, the oil sorption material may comprise a silica acid or a derivative or salt thereof such as, e.g., silicon dioxide or a polymer thereof as a pharmaceutically acceptable excipient. However, dependent on the quality employed a silicon dioxide may be a lubricant or it may be an oil sorption material. Qualities fulfilling the latter function seem to be most important.

In a specific embodiment, a composition or solid dosage form according to invention comprises a pharmaceutically acceptable excipient that is a silicon dioxide product that has properties corresponding to Aeroperl® 300

Use of an oil sorption material in compositions or dosage forms according to the invention is very advantageous for the preparation of pharmaceutical, cosmetic, nutritional and/or food compositions, wherein the composition comprises oily material. One of the advantages is that is it possible to incorporate a relatively large amount of and oily material and still have a material that is solid. Thus, it is possible to prepare solid compositions with a relatively high load of oily materials by use of an oil sorption material according to the invention. Within the pharmaceutical field it is an advantage to be able to incorporate a relatively large amount of an oily material in a solid composition especially in those situation where the active substance does not have suitable properties with respect to water solubility (e.g. poor water solubility), stability in aqueous medium (i.e. degradation occurs in aqueous medium), oral bioavailability (e.g. low bioavailability) etc., or in those situations where it is desired to modify the release of an active substance from a composition in order to obtain a controlled, delayed, sustained and/or pulsed delivery of the active substance. Thus, in a specific embodiment it is used in the preparation of pharmaceutical compositions.

The oil sorption material for use in the processing into solid compositions normally absorbs about 5% w/w or more, such as, e.g., about 10% w/w or more, about 15% w/w or more, about 20% w/w or more, about 25% w/w or more, about 30% w/w or more, about 35% w/w or more, about 40% w/w or more, about 45% w/w or more, about 50 w/w or more, about 55% w/w or more, about 60% w/w or more, about 65% w/w or more, about 70% w/w or more, about 75% w/w or more, about 80% w/w or more, about 85% w/w or more, about 90% w/w or more or about 95% w/w or more of an oil or an oily material and is still a solid material.

Oily Materials

An important aspect of the invention is compositions or solid dosage forms comprising an oily material.

In the present context the term "oily materials" is used in a very broad sense including oils, waxes, semi-solid materials and materials that normally are used as solvents (such as organic solvents) or cosolvents within the pharmaceutical industry, and the term also includes therapeutically and/or prophylactically active substances that are in liquid form at ambient temperature; furthermore the term includes emulsions like e.g. microemulsions and nanoemulsions and suspensions. The oils and oily-like materials that can be absorbed will normally be liquid at ambient or elevated temperature (for practical reasons the max. temperature is about 250° C.). They may be hydrophilic, lipophilic, hydrophobic and/or amphiphilic materials.

The oily materials that are suitable for use in the present context are substances or materials, which have a melting point of at least about 10° C. and at the most about 250° C.

In specific embodiments of the invention, the oily material has a melting point of about 5° C. or more such as, e.g., about 10° C. or more, about 15° C. or more, about 20° C. or more or about 25° C. or more.

In further embodiments of the invention, the oily material has a melting point of at least about 25° C. such as, e.g., at least about 30° C. at least about 35° C. or at least about 40° C. For practical reasons, the melting point may normally not be too high, thus, the oily material normally has a melting point of at the most about 300° C. such as, e.g., at the most about 250° C., at the most about 200° C., at the most about 150° C. or at the most about 100° C. If the melting point is higher a relatively high temperature may promote e.g. oxidation or other kind of degradation of an active substance in those cases where e.g. a therapeutically and/or prophylactically active substance is included.

In the present context, melting points are determined by DSC (Differential Scanning Calorimetry). The melting point is determined as the temperature at which the linear increase of the DSC curve intersects the temperature axis.

Interesting oily materials are in general substances, which are used in the manufacture of pharmaceuticals as so-called melt binders or solid solvents (in the form of solid dosage form), or as co-solvents or ingredients in pharmaceuticals for topical use. It may be hydrophilic, hydrophobic and/or have surface-active properties. In general hydrophilic and/or hydrophobic oily materials are suitable for use in the manufacture of a pharmaceutical composition comprising a therapeutically and/or prophylactically active substance that has a relatively low aqueous solubility and/or when the release of the active substance from the pharmaceutical composition is designed to be immediate or non-modified. Hydrophobic oily materials, on the other hand, are normally used in the manufacture of a modified release pharmaceutical composition. The above-given considerations are simplified to illustrate general principles, but there are many cases where other combinations of oily materials and other purposes are relevant and, therefore, the examples above should not in any way limit the invention.

Typically, a suitable hydrophilic oily material is selected from the group consisting of: polyether glycols such as, e.g., polyethylene glycols, polypropylene glycols; polyoxyethylenes; polyoxypropylenes; poloxamers and mixtures thereof, or it may be selected from the group consisting of: xylitol, sorbitol, potassium sodium tartrate, sucrose tribehenate, glucose, rhamnose, lactitol, behenic acid, hydroquinon monomethyl ether, sodium acetate, ethyl fumarate, myristic acid, citric acid, Gelucire 50/13, other Gelucire types such as, e.g., Gelucire 44/14 etc., Gelucire 50/10, Gelucire 62/05, Sucro-ester 7, Sucro-ester 11, Sucro-ester 15, maltose, mannitol and mixtures thereof.

A suitable hydrophobic oily material may be selected from the group consisting of: straight chain saturated hydrocarbons, sorbitan esters, paraffins; fats and oils such as e.g., cacao butter, beef tallow, lard, polyether glycol esters; higher fatty acid such as, e.g. stearic acid, myristic acid, palmitic acid, higher alcohols such as, e.g., cetanol, stearyl alcohol, low melting point waxes such as, e.g., glyceryl monostearate, glyceryl monooleate, hydrogenated tallow, myristyl alcohol, stearyl alcohol, substituted and/or unsubstituted monoglycerides, substituted and/or unsubstituted diglycerides, substituted and/or unsubstituted triglycerides, yellow beeswax, white beeswax, carnauba wax, castor wax, japan wax, acetylate monoglycerides; NVP polymers, PVP polymers, acrylic polymers, or a mixture thereof.

In an interesting embodiment, the oily material is a polyethylene glycol having an average molecular weight in a range of from about 400 to about 35,000 such as, e.g., from about 800 to about 35,000, from about 1,000 to about 35,000 such as, e.g., polyethylene glycol 1,000, polyethylene glycol 2,000, polyethylene glycol 3,000, polyethylene glycol 4,000, polyethylene glycol 5,000, polyethylene glycol 6,000, polyethylene glycol 7,000, polyethylene glycol 8,000, polyethylene glycol 9,000 polyethylene glycol 10,000, polyethylene glycol 15,000, polyethylene glycol 20,000, or polyethylene glycol 35,000. In certain situations polyethylene glycol may be employed with a molecular weight from about 35,000 to about 100,000.

In another interesting embodiment, the oily material is polyethylene oxide having a molecular weight of from about 2,000 to about 7,000,000 such as, e.g. from about 2,000 to about 100,000, from about 5,000 to about 75,000, from about 10,000 to about 60,000, from about 15,000 to about 50,000, from about 20,000 to about 40,000, from about 100,000 to about 7,000,000 such as, e.g., from about 100,000 to about 1,000,000, from about 100,000 to about 600,000, from about 100,000 to about 400,000 or from about 100,000 to about 300,000.

In another embodiment, the oily material is a poloxamer such as, e.g. Poloxamer 188, Poloxamer 237, Poloxamer 338 or Poloxamer 407 or other block copolymers of ethylene oxide and propylene oxide such as the Pluronic® and/or Tetronic® series. Suitable block copolymers of the Pluronic® series include polymers having a molecular weight of about 3,000 or more such as, e.g. from about 4,000 to about 20,000 and/or a viscosity (Brookfield) from about 200 to about 4,000 cps such as, e.g., from about 250 to about 3,000 cps. Suitable examples include Pluronic® F38, P65, P68LF, P75, F77, P84, P85, F87, F88, F98, P103, P104, P105, F108, P123, F123, F127, 10R8, 17R8, 25R5, 25R8 etc. Suitable block copolymers of the Tetronic® series include polymers having a molecular weight of about 8,000 or more such as, e.g., from about 9,000 to about 35,000 and/or a viscosity (Brookfield) of from about 500 to about 45,000 cps such as, e.g., from about 600 to about 40,000. The viscosities given above are determined at 60° C. for substances that are pastes at room temperature and at 77° C. for substances that are solids at room temperature.

The oily material may also be a sorbitan ester such as, e.g., sorbitan di-isostearate, sorbitan dioleate, sorbitan monolaurate, sorbitan monoisostearate, sorbitan monooleate, sorbitan monopalmitate, sorbitan monostearate, sorbitan sesqui-isostearate, sorbitan sesquioleate, sorbitan sesquistearate, sorbitan tri-isostearate, sorbitan trioleate, sorbitan tristearate or mixtures thereof.

The oily material may of course comprise a mixture of different oily materials such as, e.g., a mixture of hydrophilic and/or hydrophobic materials. Other suitable oily materials may be solvents or semi-solid excipients like, e.g. propylene glycol, polyglycolised glycerides including Gelucire 44/14, complex fatty materials of plant origin including theobroma oil, carnauba wax, vegetable oils like e.g. almond oil, coconut oil, corn oil, cottonseed oil, sesame oil, soya oil, olive oil, castor oil, palm kernels oil, peanut oil, rape oil, grape seed oil etc., hydrogenated vegetable oils such as, e.g. hydrogenated peanut oil, hydrogenated palm kernels oil, hydrogenated cottonseed oil, hydrogenated soya oil, hydrogenated castor oil, hydrogenated coconut oil; natural fatty materials of animal origin including beeswax, lanolin, fatty alcohols including cetyl, stearyl, lauric, myristic, palmitic, stearic fatty alcohols; esters including glycerol stearate, glycol stearate, ethyl oleate, isopropyl myristate; liquid interesterified semi-synthetic glycerides including Miglycol 810/812; amide or fatty acid alcolamides including stearamide ethanol, diethanolamide of fatty coconut acids, acetic acid esters of mono and di-glycerides, citric acid esters of mono and di-glycerides, lactic acid esters of mono and diglycerides, mono and di-glycerides, poly-glycerol esters of fatty acids, poly-glycerol poly-ricinoleate, propylene glycol esters of fatty acids, sorbitan monostearates, sorbitan tristearates, sodium stearoyl lactylates, calcium stearoyl lactylates, diacetyl tartaric acid esters of mono and di-glycerides etc.

The pharmaceutical composition or a solid dosage form according to the invention may have a concentration of the oily material in the composition or the dosage form of about 5% w/w or more such as, e.g., about 10% w/w or more, about 15% w/w or more, about 20% w/w or more, about 25% w/w or more, about 30% w/w or more, about 35% w/w or more, about 40% w/w or more, about 45% w/w or more, about 50 w/w or more, about 55% w/w or more, about 60% w/w or more, about 65% w/w or more, about 70% w/w or more, about 75% w/w or more, about 80% w/w or more, about 85% w/w or more, about 90% w/w or more or about 95% w/w or more.

In specific embodiments the concentration of the oily material in a composition or solid dosage form of the invention is in a range from about 20% to about 80% w/w such as, e.g., from about 25% to about 75% w/w.

One of the advantages is that is it possible to incorporate a relatively large amount of oily material and still have a solid material. Thus, it is possible to prepare solid compositions with a relatively high load of oily materials by use of an oil sorption material according to the invention. Within the pharmaceutical field it is an advantage to be able to incorporate a relatively large amount of an oily material in a solid composition especially in those situation where the active substance does not have suitable properties with respect to water solubility (e.g. poor water solubility), stability in aqueous medium (i.e. degradation occurs in aqueous medium), oral bioavailability (e.g. low bioavailability) etc., or in those situations where it is desired to modify the release of an active substance from a composition in order to obtain a controlled, delayed, sustained and/or pulsed delivery of the active substance.

A further advantage is that the particulate material obtained is a free-flowing powder and therefore readily processable into e.g. solid dosage forms such as tablets, capsules or sachets. Normally, the particulate material has properties that are suitable in order to manufacture tablets by direct compression without addition of large amounts of further additives. A suitable test for test the flowability of the particulate material is the method described in Ph. Eur. and measuring the flow rate of the material out of a funnel with a nozzle (orifice) diameter of 10.0 mm.

In an embodiment of the invention, at least a part of the fibrate may be present in the composition in the form of a solid dispersion including a molecular dispersion and a solid solution. Normally, 10% or more such as, e.g., 20% or more, 30% or more, 40% or more, 50% or more, 60% or more, 70% or more, 80% or more, 90% or more such as, e.g., 95% or more or about 100% w/w of the active substance thereof is present in the composition in dissolved form.

Solid Dosage Forms

The pharmaceutical composition according to the invention is in particulate form and may be employed as such. However, in many cases it is more convenient to present the composition in the form of granules, pellets, microspheres, nanoparticles and the like or in the form of solid dosage forms including tablets, tablets, beads, capsules, grains, pills, granulates, granules, powder, pellets, sachets, lozenges, troches and the like.

A solid dosage form according to the invention may be a single unit dosage form or it may in the form of a polydepot dosage form contain a multiplicity of individual units such as, e.g., pellets, beads and/or granules.

Usually, a pharmaceutical composition or a solid dosage form of the invention is intended for administration via the oral, buccal or sublingual administration route.

The invention also relates to the above-mentioned presentation form. Within the scope of the invention are compositions/solid dosage forms that are intended to release the active substance in a fast release, a delayed release or modified release manner.

A solid dosage form according to the present invention comprises a pharmaceutical composition in particulate form as described above. The details and particulars disclosed under this main aspect of the invention apply mutatis mutandis to the other aspects of the invention. Accordingly, the properties with respect to increase in bioavailability, changes in bioavailability parameters, reduction in adverse food effect as well as release of one or more fibrates etc. described and/or claimed herein for pharmaceutical compositions in particulate form are analogues for a solid dosage form according to the present invention.

Usually, the concentration of the pharmaceutical composition in particulate form is in a range of from about 5 to 100% w/w such as, e.g., from about 10% to about 90% w/w, from about 15% to about 85% w/w, from about 20% to about 80% w/w, from about 25% to about 80% w/w, from about 30% to about 80% w/w, from about 35% to about 80% w/w, from about 40% to about 75% w/w, from about 45% to about 75% w/w or from about 50% to about 70% w/w of the dosage form. In an embodiment of the invention, the concentration of the pharmaceutical composition in particulate form is 50% w/w or more of the dosage form.

The solid dosage forms of the invention are very stable. For example, the fibrate is present in an amount of at least 90%, or at least 95%, or at least 100%, relative to the amount prior to storage, when assayed after 3 months of storage at a temperature of about 40° C. and a relative humidity of about 75%. Also, the physical stability is very high as can be seen from the Examples below.

The solid dosage form according to the invention is obtained by processing the particulate material according to the invention by means of techniques well-known to a person skilled in the art. Usually, this involves further addition of one or more of the pharmaceutically acceptable excipients mentioned herein.

The composition or solid dosage form according to the invention may be designed to release one or more fibrates in any suitable manner provided that the increase in bioavailability is maintained. Thus, the active substance may be released relatively fast in order to obtain an enhanced on-set of action, it may be released so as to follow zero or first order kinetics or it may be released in a controlled or modified manner in order to obtain a predetermined pattern of release. Plain formulations are also within the scope of the present invention.

The composition or solid dosage form according to the invention may also be coated with a film coating, an enteric coating, a modified release coating, a protective coating, an anti-adhesive coating etc.

A solid dosage form according to the invention may also be coated in order to obtain suitable properties e.g. with respect to release of the active substance. The coating may be applied on single unit dosage forms (e.g. tablets, capsules) or it may be applied on a polydepot dosage form or on its individual units.

Suitable coating materials are e.g. methylcellulose, hydroxypropylmethylcellulose, hydroxypropylcellulose, acrylic polymers, ethylcellulose, cellulose acetate phthalate, polyvinyl acetate phthalate, hydroxypropyl methylcellulose phthalate, polyvinylalcohol, sodium carboxymethylcellulose, cellulose acetate, cellulose acetate phthalate, gelatin, methacrylic acid copolymer, polyethylene glycol, shellac, sucrose, titanium dioxide, carnauba wax, microcrystalline wax, zein.

Plasticizers and other ingredients may be added in the coating material. The same or different active substance may also be added in the coating material.

The pharmaceutical composition or a solid dosage form according to the invention is designed to release the fibrate in a suitable manner. Specific release patterns are disclosed in the appended claims to which reference is made. Herein is also given specific relevant absorption patterns.

Other Embodiments of the Invention

In yet another aspect, the invention relates to a solid pharmaceutical composition in particulate form comprising one or more fibrates and one or more oily materials, the composition having a suitable flowability as determined according to the method described in Ph. Eur. measuring the flow rate of the composition out of a funnel with a nozzle diameter of 10.0 mm. In order to avoid any adherence to the manufacturing and/or filling equipment it is important that the particulate material is freely flowing. This characteristic is also important in those cases where it is desired to process the particulate material further into other kinds of formulations such as, e.g., solid dosage forms.

Yet another aspect of the invention relates to a solid pharmaceutical composition in particulate form comprising one or more fibrates, one or more oily materials and one or more oil-sorption materials, which i) has an oil threshold value of 10% or more, when tested according to the Threshold Test herein, and fulfills at least one of ii) releases at least 30% of an oil, when tested according to the Release Test herein, and iii) in the form of a tablet has a disintegration time of at the most 1 hour, when tested according to Ph. Eur. Disintegration test, the tablet containing about 90% w/w or more of the oil-sorption material. In certain situations, it has been found that it is an advantage to incorporate a sorption material in the composition in order e.g. to enable a high concentration of an oily material. In those cases where the oily material has a melting point of at the most about 250° C., it may be especially suitable to incorporate a sorption material. Suitable examples of oily materials as well as sorption materials are given herein.

In a further specific embodiment, the fibrate is present at least partly in the form of a solid dispersion including a solid solution.

In a further embodiment, the present invention relates to a solid pharmaceutical composition in particulate form or a solid dosage form comprising one or more fibrates dissolved in one or more oily materials. In this aspect, the fibrate is present in the form of a solid solution in the particulate composition and the presence of a solid solution can be tested by the DSC test mentioned herein. In this aspect, the particulate composition is prepared by dissolving the fibrate in an oily material optionally at elevated temperature and (optionally after addition of further active substances and/or one or more pharmaceutically acceptable excipients) the mixture is sprayed on a carrier as described herein. Preferably, the concentration of the oily material is at least about 10% w/w.

Materials and Methods

Materials

Fenofibrate (supplied by Sigma)
Lactose monohydrate 200 mesh (from DMV)
Granulated silicium oxide, Aeroperl® 300, (Degussa)
Polyethylene glycol 6000, Pluracol® E6000 (from BASF)
Poloxamer 188, Pluronic® F-68 (from BASF)
Glyceryl monostearate, Rylo® MD50, (from Danisco Cultor), Ph. Eur.
Avicel PH200 (microcrystalline cellulose) (from FMC)
Magnesium Stearate Tablets, capsules or granules might be enteric coated with different types of polymers such as hydroxypropylmethylcellulose acetate succinate (Aqoat), cellulose acetate phthalate CAP, hydroxypropylmethylcellulose phtalate HPMCP or methacrylic acid copolymers such as Eudragit L30D, Eudragit 100/S, Eudragit 100/L.

Tricor Tablet Formulation

TRICOR® tablets are fenofibrate-containing tablets available for oral administration, either containing 54 mg or 160 mg of micronized fenofibrate per tablet.

The tablets contain the following inactive ingredients: colloidal silicon dioxide, crospovidone, lactose monohydrate, lecithin, microcrystalline cellulose, polyvinyl alcohol, povidone, sodium lauryl sulfate, sodium stearyl fumarate, talc, titanium dioxide, xanthan gum, colorant. Tricor is indicated as a lipid regulating agent. The recommended dosage of Tricor® is 54-160 mg/day taken with food. Tricor® tablets are provided in strengths of 54 and 160 mg, whereas Tricor® capsules are provided in strengths of 67 and 200 mg. The tablets have a higher bioavailability than the capsules. Other trade names are Lipanthyl®, Lipantil® or Catalip®.

Lipanthyl Formulation

Lipanthyl®67M results from a process in which fenofibrate is co-micronized with a solid surface-active component to give an intimate and finely divided mixture of the two ingredients.

Equipment

Laboratory scale fluid bed equipment: Strea-1.

The melt feed unit is a prototype composed of separate units for heating of air supplies for the atomizer, pressure tank and feeding tube. Granulate was sieved manually and mixed with extragranular excipients in a Turbula mixer.

Tablet compression was performed on a single punch press, Diaf TM20.

Methods

According to the method of the invention, the fenofibrate drug was dissolved into the melted vehicle(s) and applied on the particulate carrier(s) as follows:

The vehicle(s) was melted in a beaker placed in a microwave oven. The beaker was transferred to a temperature controlled heating plate supplied with magnetic stirring. Fenofibrate was dissolved slowly in the melt at a temperature of 75° C. under magnetic stirring. The hot solution was transferred to the pressure tank for melt spray application onto the carrier in the fluid bed. The granulate product was discharged from the fluid bed and sieved through sieve 0.7 mm or 1.0 mm manually. The sieved product was blended with magnesium stearate for 0.5 min in a Turbula mixer. If an extragranular phase has to be incorporated, the extragranular phase was premixed with the granulate in 3 minutes in a Turbula mixer.

The tablet compression was performed on a single punch machine Diaf TM20.

Threshold Test

The test involves determination of flowability according to the method described in Ph. Eur. by measuring the flow rate of the material out of a funnel with a nozzle diameter of 10.0 mm.

Viscoleo (medium chain triglycerides MCT; Miglyol 812 N from Condea) was added to 100 g of the solid pharmaceutically acceptable material to be tested for use according to the invention and mixed manually. The mixture obtained was sieved through sieve 0.3 mm to assure a homogenous mixture. The oil was added successively until a flow of 100 g of the mixture could not flow through the nozzle. If the material to be tested has a high bulk volume (e.g. like that of Aeroperl 300) only 50 g of the mixture is used when testing these blends. The maximal concentration of oil where flow of material could be obtained is called the Threshold Value (given as % w/w).

Release Test

A fat-soluble colorant Sudan II (BDH Gur®) obtained from BDH VWR International 14.3 mg was dissolved in 50.0 g viscoleo (fractionated medium chain triglycerides).

10 g of the oil was added to 10.0 g of the solid pharmaceutically acceptable material to be tested for use according to the present invention and mixed until the oil was fully absorbed in the solid material. The mixture was subsequently sieved through sieve 0.3 mm to achieve a homogeneous mixture.

1.00 g of the mixture was transferred to a centrifugal tube and 3.00 ml of water was added. The suspension was mixed in a blood sample turner for 1 hour and subsequently centrifuged for 10 minutes at 5000 rpm. The upper phase of oil and water was transferred carefully to a beaker and the water was evaporated in an oven at 80° C. until constant weight. The amount of oil released from the solid material was calculated on basis of the weight of the remaining after evaporation of the water phase.

Disintegration Test

The disintegration time was determined according to the method described in to Ph. Eur.

Dissolution Test

The test was performed in accordance with Ph. Eur 2.9.3 using the paddle apparatus. The quantification was performed using HPLC with UV-detection.

| | |
|---|---|
| Medium: | 900 ml water with 0.75% sodium lauryl sulfate (SLS) |
| Rotation speed: | 50 rpm |
| Temperature: | 37° C. |
| Sampling time: | 10, 20, 30, 45 and 60 minutes |
| Acceptance criteria: | >75% at 45 minutes |

Determination of Bulk Density

The bulk density was measured by pouring 100 g of the powder in question in a 250 ml graduated cylinder. The bulk density is given as the tapped bulk density in g/ml. The determination was performed according to Ph. Eur. (apparent volume).

Determination of Oil Absorption Value

The oil absorption value is determined by adding well-defined amounts (a 10 g) of viscoleo to a well-defined amount of the pharmaceutically acceptable material (100 g) to be tested. The oil absorption value (expressed as g viscoleo/100 g material) is reached when a further addition of 10 g oil results in a material that does not have suitable properties with respect to flowability, i.e. the material does not meet the meet the requirements when tested according to Ph. Eur. (flowability test; see above under Threshold Test herein).

Determination of BET Surface Area

The apparatus applied was a Micromertics Gemini 2375. The method applied was according to USP volumetric methods based on multiple point determination.

Determination of Flowability

The flowability was determined according to the method described in Ph. Eur. measuring the flow rate of the material out of a funnel with a nozzle diameter of 10.0 mm.

Determination of Weight Variation

The tablets prepared in the Examples herein were subject to a test for weight variation performed in accordance with Ph. Eur.

Determination of Average Tablet Hardness

The tablets prepared in the Examples herein were subject to at test for tablet hardness employing Schleuniger Model 6D apparatus and performed in accordance with the general instructions for the apparatus.

Determination of Solid Solution

According to the present invention, the fibrate is dissolved in a vehicle. In order to substantiate this, a test involving differential scanning calometry is performed. The test is performed on the particulate composition, solid dosage form or mixture of vehicle and fibrate (after the solid solution is supposed to form). Standard DSC equipment connected to a PC is used.

| | |
|---|---|
| Sample size: | 10 mg in alu pans |
| Heating rate: | 5° C./min from 27° C. to 110° C. |
| Evaluation: | The fibrate is considered to be in dissolved state or non-crystalline if no fibrate endoterm peak is observed and if the melting interval does not significantly shift compared with the vehicle alone. |

Determination of Geometric Weight Mean Diameter $d_{gw}$

The geometric weight mean diameter was determined by employment of a method of laser diffraction dispersing the particulate material obtained (or the starting material) in air. The measurements were performed at 1 bar dispersive pressure in Sympatec Helos equipment, which records the distribution of the equivalent spherical diameter. This distribution is fitted to a log normal volume-size distribution. When used herein, "geometric weight mean diameter" means the mean diameter of the log normal volume-size distribution.

In Vivo Studies in Beagle Dogs

In vivo studies with the purpose of determining the bioavailability of the compositions of the present invention relative to the bioavailability of the commercially available fenofibrate tablet formulation, i.e. Tricor®, was performed using Beagle dogs.

The experimental work was performed in Denmark using four male Beagle dogs each having a body weight of 12-18 kg (starting weight). The studies were conducted as open, non-randomised, cross-over studies. Each animal was its own control. Oral doses of fenofibrate was administered according to the data below. The dogs were fasted overnight prior to dosing (water ad libitum) and were fed 5 hours after dosing (water ad libitum). Each dog was dosed with the specified dose of fenofibrate without taking the weight of the dog into consideration.

Blood samples were collected at vena jugularis externa at the following points of time: Pre-dose, 1, 1.5, 2, 3, 4, 6, 8, 12 and 24 hours after dosing. 4 ml of blood were collected, mixed with EDTA, and the samples were frozen (−80° C.). The blood samples were analyzed using on-line extraction LC/MS and results were given in mg/mL. The determined full blood concentration profiles of fenofibrate were treated using the Pharmacokinetic softwear WinNonlin®, (Pharsight, Calif.; USA) to calculate the pharmacokinetic parameters. All data are dose adjusted, when necessary.

The following examples serve the purpose of illustration of the invention and are not intended to limiting the scope of the present invention. Pharmaceutical compositions and dosage forms of the invention are exemplified in examples 1-7. Results of in vitro dissolution tests of dosage forms of the invention are found in example 8. Results of stability tests of dosage forms of the invention are found in example 9. Results of in vivo comparison studies in Beagle dogs (blood plasma concentration) are found in example 10-12.

Example 1

Immediate Release Tablet with Improved Bioavailability

Fenofibrate was dissolved at a concentration of 17% in polyethylene glycol 6000 and Poloxamer 188 (70:30 w/w ratio) at 75° C. 244 g of the melted solution was sprayed on 200 g lactose in a fluid bed Strea-1 at 75° C. The granular product was sieved through sieve 0.7 mm and blended with magnesium stearate for 0.5 min in a Turbula mixer. The mixture was compressed into 10 mm tablets with a strength of 50 mg (540 mg tablet with compound cup shaped).

| Substance | % | mg |
|---|---|---|
| Fenofibrate | 9.30 | 50.00 |
| Lactose | 44.78 | 240.64 |
| PEG 6000 | 31.80 | 170.88 |
| Poloxamer 188 | 13.63 | 73.24 |
| Magnesium stearate | 0.50 | 2.69 |
| Total | 100.00 | 537.45 |

Mean disintegration time: 26 min, Hardness: 45 N

Example 2

Immediate Release Tablet with Improved Bioavailability 10 mm tablets of 50 mg strength (540 mg tablet with compound cup shaped) and having the following composition were prepared as described in Example 1:

| Substance | % | mg |
|---|---|---|
| Fenofibrate | 9.30 | 50.00 |
| Lactose | 44.78 | 240.64 |
| PEG 6000 | 45.43 | 244.12 |
| Magnesium stearate | 0.50 | 2.69 |
| Total | 100.00 | 537.45 |

Mean disintegration time: 21 min, Hardness: 55 N

Example 3

Immediate Release Tablet with Improved Bioavailability 10 mm tablets of 50 mg strength (540 mg tablet with compound cup shaped) and having the following composition were prepared as described in Example 1:

| Substance | % | mg |
|---|---|---|
| Fenofibrate | 9.30 | 50.00 |
| Lactose | 44.78 | 240.64 |
| PEG 4000 | 31.80 | 170.88 |
| Poloxamer 188 | 13.63 | 73.24 |
| Magnesium stearate | 0.50 | 2.69 |
| Total | 100.00 | 537.45 |

Mean disintegration time: 22 min, Hardness: 48 N

Example 4

Immediate Release Tablet with Improved Bioavailability

Fenofibrate was dissolved in polyethylene glycol 4000 in a concentration of 17% at 75° C. 244 g of the melted solution was sprayed on 200 g lactose in a fluid bed Strea-1 at 75° C. The granular product was sieved through sieve 0.7 mm and blended with magnesium stearate for 0.5 min in a Turbula mixer. The mixture was compressed into 10 mm tablets of 50 mg strength (540 mg tablet with compound cup shaped).

| Substance | % | mg |
|---|---|---|
| Fenofibrate | 9.30 | 50.00 |
| Lactose | 44.78 | 240.64 |
| PEG 4000 | 45.43 | 244.12 |
| Magnesium stearate | 0.50 | 2.69 |
| Total | 100.00 | 537.45 |

Mean disintegration time: 21 min, Hardness: 55 N

Example 5

Immediate Release Tablet with Improved Bioavailability

Fenofibrate was dissolved in polyethylene glycol 4000 in a concentration of 17% at 75° C. 244 g of the melted solution was sprayed on 190 g lactose in mixture with 10 g sodium lauryl sulfate (SDS) in a fluid bed Strea-1 at 75° C. The granular product was sieved through sieve 0.7 mm and blended with magnesium stearate for 0.5 min in a Turbula mixer. The mixture was compressed into 10 mm tablets of 50 mg strength (540 mg tablet with compound cup shaped).

| Substance | % | mg |
|---|---|---|
| Fenofibrate | 9.30 | 50.00 |
| Lactose | 42.54 | 228.61 |
| SDS | 2.23 | 12.03 |
| PEG 4000 | 45.43 | 244.12 |
| Magnesium stearate | 0.50 | 2.69 |
| Total | 100.00 | 537.45 |

Mean disintegration time: 18 min, Hardness: 65 N

Example 6

Immediate Release Tablet with Improved Bioavailability

Fenofibrate was dissolved in a concentration of 30% in polyethylene glycol 4000 and Poloxamer 188 (70:30 w/w ratio) at 75° C. 466 g of the melted solution was sprayed on 200 g Aeroperl 300 in a fluid bed Strea-1 at 75° C. The granular product was sieved through sieve 0.7 mm and blended with magnesium stearate for 0.5 min in a Turbula mixer. The mixture was compressed into 13.5 mm tablets of 150 mg strength (720 mg tablet with compound cup shaped).

| Substance | % | mg |
|---|---|---|
| Fenofibrate | 20.90 | 150.00 |
| Aeroperl 300 | 29.85 | 214.29 |
| PEG 6000 | 34.13 | 245.00 |
| Poloxamer 188 | 14.63 | 105.00 |
| Mg-stearat | 0.50 | 3.59 |
| Total | 100.00 | 717.88 |

Mean disintegration time: 35 min, Hardness: 35 N

Example 7

Formulations of the Invention

Tablets of 50 mg and 160 mg strength, respectively and having the following compositions were prepared as described in Examples 1, 4 and 6:

| Substance | Ingredient | A mg | B mg | C mg | D mg | E mg |
|---|---|---|---|---|---|---|
| Drug | Fenofibrate | 160.09 | 50.05 | 50.08 | 50.09 | 159.99 |
| Vehicle 1 | PEG6000 | 208.12 | 171.09 | 124.29 | — | — |
|  | PEG4000 | — | — | — | 244.57 | — |
|  | GMS (Rylo) | — | — | — | — | 86.15 |
| Vehicle 2 | Poloxamer188 | 89.19 | 73.33 | 53.27 | — | — |
| Carrier | Lactose | 356.51 | 231.87 | — | 232.02 | 163.01 |
|  | Aeropearl 300 | — | — | 63.89 | — | — |
| Excipients | Mg stearate | 4.09 | 2.65 | 1.47 | 5.32 | 8.35 |
|  | Avicel | — | — | — | — | 417.50 |
| Total |  | 818.00 | 529.00 | 293.00 | 532.00 | 835.00 |
| Hardness | N | 60 | 44 | 44 | 47 | 102 |
| Disintegration time | Minutes | 25 | 14 | 30 | 48 | >55 |
| Diameter | Mm | Oblong | 12 | 12 | 10 | Oblong |

Example 8

Dissolution Tests

The inventive tablet formulation A of example 7 was subjected to a dissolution test as described in Methods with the following results:

| Time (min) | % dissolved |
|---|---|
| 0 | 0 |
| 10 | 28 |
| 20 | 56 |
| 30 | 74 |
| 45 | 88 |
| 60 | 97 |

Example 9

Stability Tests

Samples of the inventive tablet formulation A of example 7 was stored under the following conditions, respectively, and subjected to a dissolution (stability) test as described in Methods after 1 month and 3 months of storage; % dissolved is the percentage of fenofibrate dissolved after 45 minutes:

| | % dissolved | | |
|---|---|---|---|
| Months | 25° C. and 60% RH | 30° C. and 65% RH | 40° C. and 75% RH |
| 0 | 88 | — | — |
| 1 | 99 | 88 | 90 |
| 3 | 90 | 97 | 90 |

Samples of the inventive tablet formulation A of example 7 was stored under the following conditions, respectively, and subjected to a fibrate assay with the following results:

| | mg fenofibrate | | |
|---|---|---|---|
| Months | 25° C. and 60% RH | 30° C. and 65% RH | 40° C. and 75% RH |
| 0 | 163.8 | — | — |
| 1 | 161.9 | 160.1 | 160.8 |
| 3 | 162.6 | 164.9 | 164.4 |

Samples of the inventive tablet formulation A of example 7 was stored under the following conditions, respectively, and subjected to a degradation product test according to Ph. Eur. (Degradation products A, B, G and Unknown accumulated into Total Degradation Product; HPLC method) with the following results:

| | Total Degradation Product, % w/w, impurity | | |
|---|---|---|---|
| Months | 25° C. and 60% RH | 30° C. and 65% RH | 40° C. and 75% RH |
| 0 | 0.05 | — | — |
| 1 | 0.05 | 0.05 | 0.05 |
| 3 | 0.05 | 0.05 | 0.05 |

Example 10

In Vivo Study in Dogs

An in vivo study of formulation A of example 7, 160 mg in Beagle dogs, performed as described above under Methods, relative to Tricor®, 160 mg (Batch no.: 098212E21), gave the following results:

Blood concentrations (mg/mL) (average of 4 dogs) after administration of formulation:

| | Formulation | |
|---|---|---|
| Time (hr) | Tricor ® (160 mg) | Invention, A (160 mg) |
| 0 | n.a. | n.a. |
| 0.5 | 367.5 | 995.8 |
| 1.0 | 612.5 | 2209.3 |
| 1.5 | 722.0 | 2627.8 |
| 2.0 | 725.8 | 2097.3 |
| 3.0 | 443.8 | 1219.5 |
| 4.0 | 295.3 | 930.5 |
| 6.0 | 160.5 | 642.0 |
| 8.0 | 250.3 | 869.5 |
| 12.0 | 211.8 | 615.3 |
| 24.0 | 133.3 | 394.0 |
| 48.0 | n.a. | 164.5 |

Relative bioavailability based on AUC (invention, A/Tricor®): 306%.
Relative $c_{max}$ (invention, A/Tricor®): 356%.

Example 11

In Vivo Study in Dogs

A second in vivo study of formulation A of example 7, 160 mg in Beagle dogs, performed as described above under Methods, relative to Tricor®, 160 mg (Batch no.: 098212E21), gave the following results:

Blood concentrations (mg/mL) (average of 4 dogs) after administration of formulation:

| | Formulation | |
|---|---|---|
| Time (hr) | Tricor ® (160 mg) | Invention, A (160 mg) |
| 0 | 0 | 0 |
| 0.5 | 339.3 | 3616.0 |
| 1.0 | 1318.8 | 3724.8 |
| 1.5 | 1313.3 | 2982.0 |
| 2.0 | 1390.0 | 2355.8 |
| 3.0 | 1361.3 | 1359.5 |
| 4.0 | 1019.3 | 1309.5 |
| 6.0 | 969.3 | 973.8 |
| 8.0 | 667.0 | 1113.0 |
| 12.0 | 390.3 | 768.5 |
| 24.0 | 183.3 | 295.0 |
| 48.0 | 85.0 | 302.0 |

Relative bioavailability based on AUC (invention, A/Tricor®): 198%.
Relative $c_{max}$ (invention, A/Tricor®): 238%.

Example 12

In Vivo Study in Dogs

An in vivo study of the formulations B, C and D of example 7, 2x50 mg in Beagle dogs, performed as described above under Methods, relative to Lipanthyl® 67M, 2×67 mg (Batch no.: 75641), gave the following results:
Blood concentrations (mg/mL) (average of 4 dogs) after administration of formulation:

| | Formulation | | | |
|---|---|---|---|---|
| Time (hr) | Lipanthyl ® 67M (2 × 67 mg) | Invention, B (2 × 50 mg) | Invention, C (2 × 50 mg) | Invention, D (2 × 50 mg) |
| 0 | 0 | 0 | 0 | 0 |
| 0.5 | 187.3 | 2769.5 | 227.3 | 546.0 |
| 1.0 | 669.5 | 3526.8 | 521.5 | 1381.5 |
| 1.5 | 960.3 | 3106.3 | 858.3 | 1615.5 |
| 2.0 | 895.3 | 2938.0 | 989.3 | 1566.8 |
| 3.0 | 433.0 | 2465.5 | 902.5 | 1503.3 |
| 4.0 | 240.0 | 1492.3 | 783.8 | 1719.0 |
| 6.0 | 77.8 | 809.5 | 655.8 | 1034.5 |
| 8.0 | 79.3 | 1202.8 | 409.0 | 1056.0 |
| 12.0 | 291.3 | 848.0 | 269.8 | 597.3 |
| 24.0 | 82.5 | 378.0 | 163.8 | 282.8 |
| 48.0 | 19.3 | 18.8 | 51.5 | 36.5 |
| 72.0 | 0 | 0 | 0 | 0 |

Relative bioavailability based on AUC (invention, B/Lipanthyl®67M): 532%.
Relative $c_{max}$ (invention, BA/Lipanthyl® 67M): 548%.
Relative bioavailability based on AUC (invention, C/Lipanthyl®67M): 228%.
Relative $c_{max}$ (invention, C/Lipanthyl®67M): 161%.
Relative bioavailability based on AUC (invention, D/Lipanthyl® M): 424%.
Relative $c_{max}$ (invention, D/Lipanthyl®67M): 329%.

The invention claimed is:

1. A tablet comprising particles comprising (a) a solid carrier and (b) fenofibrate in a vehicle, the vehicle having a melting point of from about 30° C. to about 100° C., wherein
    the particles have a $d_{gw}$ of from about 20 μm to about 2000 μm,
    the particles comprise about 10% to about 70% by weight of fenofibrate, based upon 100% total weight of the fenofibrate and vehicle, and
    the tablet provides immediate release of the fenofibrate.

2. The tablet of claim 1, wherein the particles have a $d_{gw}$ of from about 100 to about 400 μm.

3. The tablet of claim 1, wherein the vehicle has a melting point of from about 40° C. to about 75° C.

4. The tablet of claim 3, wherein the vehicle has a melting point of from about 40° C. to about 70° C.

5. The tablet of claim 1, wherein the vehicle is hydrophilic.

6. The tablet of claim 1, wherein the vehicle comprises one or more of polyethylene glycol, poloxamers, polyoxyethylene stearates, poly-epsilon-caprolactone, polyvinylpyrrolidone, polyvinylpyrrolidone-polyvinylacetate copolymer, polymethacrylic polymers, polyvinyl alcohol, hydroxypropyl cellulose, hydroxypropyl methyl cellulose, methyl cellulose, and poly(ethylene oxide).

7. The tablet of claim 1, wherein the vehicle comprises one or more of polyvinylpyrrolidones, polyvinyl-polyvinylacetate copolymers, polyvinyl alcohol, polyvinylpyrrolidone polymers, acrylic polymers, polymethacrylic polymers, myristyl alcohol, hydroxypropyl methylcellulose, hydroxypropyl cellulose, methylcellulose, sodium carboxymethylcellulose, hydroxyethyl cellulose, pectins, cyclodextrins, galactomannans, alginates, carragenates, xanthan gums and mixtures thereof.

8. The tablet of claim 1, wherein the vehicle comprises polyoxyethylene oxide, polyoxyethylene stearate, poly-epsilon-caprolactone or any mixtures thereof.

9. The tablet of claim 1, wherein the vehicle comprises poloxamer.

10. The tablet of claim 9, wherein the poloxamer is poloxamer 188.

11. The tablet of claim 9, wherein the poloxamer is poloxamer 407.

12. The tablet of claim 9, wherein the weight ratio of fenofibrate to poloxamer is from about 3:1 to about 1:20.

13. The tablet of claim 1, wherein the tablet is a compressed tablet.

14. The tablet of claim 1, wherein at least 75% of the fenofibrate is released within about 45 minutes when tested according to Ph. Eur. Dissolution test (paddle) employing water with 0.75% sodium lauryl sulfate as the dissolution medium and at 50 rpm and a temperature of about 37° C.

15. A solid dosage form comprising particles, the particles comprising a solid carrier sprayed with fenofibrate in a vehicle, the vehicle having a melting point of from about 30° C. to about 100° C., wherein
    the solid dosage form comprises about 10% to about 70% by weight of fenofibrate, based upon 100% total weight of the fenofibrate and vehicle,
    the particles have a $d_{gw}$ of from about 20 μm to about 2000 μm, and
    the solid dosage form provides immediate release of the fenofibrate.

16. The solid dosage form of claim 15, wherein the particles have a $d_{gw}$ of from about 100 μm to about 400 μm.

17. The solid dosage form of claim 15, wherein the vehicle has a melting point of from about 40° C. to about 75° C.

18. The solid dosage form of claim 15, wherein the vehicle comprises poloxamer.

19. A solid dosage form prepared by:
    (a) spraying a mixture of fenofibrate and a liquid vehicle onto a solid carrier to form particles, said solid carrier at a temperature below the melting point of the vehicle, wherein the vehicle has a melting point of from about 30° C. to about 100° C.; and
    (b) forming a solid dosage from the particles of step (a), wherein
    the particles have a $d_{gw}$ of from about 20 μm to about 2000 μm,
    the solid dosage form comprises from about 10% to about 70% by weight of fenofibrate, based upon 100% total weight of the fenofibrate and vehicle, and
    the solid dosage form provides immediate release of the fenofibrate.

20. The solid dosage form of claim 19, wherein the particles have a $d_{gw}$ of from about 100 μm to about 400 μm.

21. The solid dosage form of claim 19, wherein the vehicle having a melting point of from about 40° C. to about 75° C.

22. A tablet comprising fenofibrate in a vehicle, the vehicle comprising poloxamer, wherein
    (i) the tablet comprises about 10% to about 35% by weight of fenofibrate, based upon 100% total weight of the fenofibrate and vehicle,
    (ii) the tablet is prepared by (a) spraying a mixture of fenofibrate and poloxamer onto a solid carrier, and (b) forming a tablet form the product of step (a), and
    (iii) the tablet provides immediate release of the fenofibrate.

23. A method of reducing total cholesterol (total-C), LDL-C, apo-lipoprotein B, or total triglycerides in a patient in need thereof, the method comprising orally administering a tablet of claim 1 to said patient.

24. The tablet of claim 1, wherein the vehicle comprises polyethylene glycol.

25. The solid dosage form of claim 15, wherein the vehicle comprises polyethylene glycol.

26. The solid dosage form of claim 19, wherein the vehicle comprises polyethylene glycol.

27. The tablet of claim 1, wherein the vehicle comprises hydrogenated castor oil.

28. The solid dosage form of claim 15, wherein the vehicle comprises hydrogenated castor oil.

29. The solid dosage form of claim 19, wherein the vehicle comprises hydrogenated castor oil.

* * * * *